United States Patent
Hellerbrand et al.

(10) Patent No.: US 8,372,419 B2
(45) Date of Patent: Feb. 12, 2013

(54) COATED IMPLANTS, THEIR MANUFACTURING AND USE THEREOF

(75) Inventors: Klaus Hellerbrand, Geltendorf (DE); Michael Siedler, Munich (DE); Andreas Schutz, Kreiling (DE); Bernd Schimkat, Munich (DE); Karin Wiedenmann-Schlembach, Planegg (DE)

(73) Assignee: Scil Technology GmbH, Planegg (DE)

( * ) Notice: Subject to any disclaimer, the term of this patent is extended or adjusted under 35 U.S.C. 154(b) by 805 days.

(21) Appl. No.: 10/598,698

(22) PCT Filed: Mar. 9, 2005

(86) PCT No.: PCT/EP2005/002506
§ 371 (c)(1), (2), (4) Date: Sep. 8, 2006

(87) PCT Pub. No.: WO2005/089829
PCT Pub. Date: Sep. 29, 2005

(65) Prior Publication Data
US 2007/0202144 A1  Aug. 30, 2007

(30) Foreign Application Priority Data
Mar. 10, 2004  (EP) .................................... 04005708

(51) Int. Cl.
*A61F 2/02* (2006.01)
*B05D 3/02* (2006.01)

(52) U.S. Cl. ...................................... 424/423; 427/2.24
(58) Field of Classification Search .......................... None
See application file for complete search history.

(56) References Cited

U.S. PATENT DOCUMENTS

| | | | |
|---|---|---|---|
| 4,051,598 A | 10/1977 | Sneer | |
| 4,063,367 A * | 12/1977 | Talalay | 34/410 |
| 4,599,085 A | 7/1986 | Riess et al. | |
| 4,882,196 A | 11/1989 | Shimamune et al. | |
| 5,011,691 A | 4/1991 | Oppermann et al. | |
| 5,258,029 A | 11/1993 | Chu et al. | |
| 5,266,683 A | 11/1993 | Oppermann et al. | |
| 5,316,146 A * | 5/1994 | Graff | 206/438 |
| 5,335,769 A * | 8/1994 | Klokkers-Bethke et al. | 206/438 |
| 5,344,654 A | 9/1994 | Rueger et al. | |
| 5,571,523 A * | 11/1996 | Lee et al. | 424/423 |
| 5,697,997 A | 12/1997 | Aronsson et al. | |
| 5,934,287 A | 8/1999 | Hayashi et al. | |
| 6,113,993 A * | 9/2000 | Gao et al. | 427/573 |
| 6,129,928 A | 10/2000 | Sarangapani et al. | |
| 6,312,472 B1 | 11/2001 | Hall et al. | |
| 6,322,728 B1 | 11/2001 | Brodkin et al. | |
| 6,419,708 B1 | 7/2002 | Hall et al. | |
| 6,994,549 B2 | 2/2006 | Brodkin et al. | |
| 2003/0204239 A1 | 10/2003 | Carlyle et al. | |

FOREIGN PATENT DOCUMENTS

| | | |
|---|---|---|
| DE | 2928007 A1 | 1/1981 |
| EP | 0584283 B1 | 12/1991 |
| EP | 0478532 A1 | 4/1992 |
| EP | 0389713 B1 | 4/1993 |
| EP | 0467948 B1 | 1/1996 |
| EP | 0362367 B1 | 2/1996 |
| EP | 0372031 B1 | 9/1996 |
| EP | 0679097 B1 | 5/1997 |
| EP | 0657146 B1 | 4/1998 |
| EP | 0448704 B1 | 6/1998 |
| EP | 0643767 81 | 7/1998 |
| EP | 0548365 B1 | 3/1999 |
| EP | 0601106 B1 | 5/2000 |
| EP | 0812207 81 | 11/2000 |
| EP | 0575555 B1 | 7/2001 |
| EP | 0739191 B1 | 1/2002 |
| EP | 1221484 A2 | 7/2002 |
| EP | 1225225 A2 | 7/2002 |
| EP | 0806211 81 | 10/2002 |
| EP | 0714665 B1 | 1/2003 |
| EP | 1251889 B1 | 2/2003 |
| EP | 1223990 B1 | 7/2004 |
| EP | 1220693 B1 | 12/2004 |
| EP | 1150725 B1 | 6/2005 |
| EP | 0972520 B1 | 8/2005 |
| EP | 0646022 B1 | 9/2005 |
| EP | 0601135 81 | 11/2005 |
| EP | 0723013 B1 | 6/2006 |
| WO | WO 8800205 | 1/1988 |

(Continued)

OTHER PUBLICATIONS www.science.unitn.it/~gcsmfo/facilities/dip-coating.htm (published: Oct. 22, 2004).*

(Continued)

*Primary Examiner* — Dennis Heyer
(74) *Attorney, Agent, or Firm* — Norman B. Thot

(57) ABSTRACT

The present invention relates to a method of coating of a device, preferably implants, with a substance comprising the steps of (a) contacting said device into a solution of said substrate or substance, and (b) drying said device while being submerged in said solution. The present invention also relates to a packaging container for a device, preferably an implant. Said packaging container being adapted such that said device is coatable within said packaging container. Moreover, the present invention relates to a method of coating the inner surfaces of a packaging container for a device, preferably implants, to be coated by a substance, comprising the steps of (a) siliconizing said inner surfaces of said container using a silicone emulsion, and (b) heat-curing to form a baked-in silicone layer on said inner surfaces of said container.

17 Claims, 14 Drawing Sheets

FOREIGN PATENT DOCUMENTS

| WO | WO 9200382 | | 1/1992 |
|---|---|---|---|
| WO | WO 9300432 | | 1/1993 |
| WO | WO 9316099 | | 8/1993 |
| WO | WO 9410203 | | 5/1994 |
| WO | WO 9415949 | | 7/1994 |
| WO | WO 9415966 | | 7/1994 |
| WO | WO 9421681 | | 9/1994 |
| WO | WO 9426892 | | 11/1994 |
| WO | WO 9426893 | | 11/1994 |
| WO | WO 9501801 | | 1/1995 |
| WO | WO 9510539 | | 4/1995 |
| WO | WO 9513101 | | 5/1995 |
| WO | WO 9516035 | | 6/1995 |
| WO | WO 9533830 | | 12/1995 |
| WO | WO 9601316 | | 1/1996 |
| WO | WO 9601845 | | 1/1996 |
| WO | WO 9610370 | | 4/1996 |
| WO | WO 9614335 | | 5/1996 |
| WO | WO 9636710 | | 11/1996 |
| WO | WO 9741273 | | 11/1997 |
| WO | WO 9843550 | | 10/1998 |
| WO | WO 9848862 | | 11/1998 |
| WO | WO 0072776 A1 | | 12/2000 |
| WO | WO 0072777 A1 | | 12/2000 |
| WO | WO 0072778 A1 | | 12/2000 |
| WO | WO 0197679 A2 | | 12/2001 |
| WO | WO 0209788 A1 | | 2/2002 |
| WO | WO03/043673 | * | 5/2003 |
| WO | WO 0343673 A1 | | 5/2003 |
| WO | WO 03043673 | * | 5/2003 |
| WO | 03/090809 A1 | | 11/2003 |
| WO | WO 2005016399 | * | 2/2005 |
| WO | WO 2005016399 A | | 2/2005 |

OTHER PUBLICATIONS

Wharton et al., "*Drosophilia* 60A gene, another transforming growth factor β family member, is closely related to human bone morphogenetic proteins," *Proc. Natl. Acad. Sci. USA.*, vol. 88, pp. 9214-9218, 1991.

Shah et al., "Mechanism of BMP-2 stimulated adhesion of osteoblastic cells to titanium alloy," *Biology of the Cell*, vol. 91, pp. 131-142, 1999.

Wozney et al., "Bone Morphogenetic Protein and Bone Morphogenetic Protein Gene Family in Bone Formation and Repair," *Clinical Orthopaedics and Related Research*, No. 346, pp. 26-37, 1998.

Wozney et al., "Novel Regulators of Bone Formation: Molecular Clones and Activities," *Science*, vol. 242, pp. 1528-1534, 1988.

Weeks et al., "A Maternal mRNA Localized to the Vegetal Hemisphere in Xenopus Eggs Codes for a Growth Factor Related to TGF-β," *Cell*, vol. 51, pp. 861-867, 1987.

Voggenreiter et al., " Assesment of the Biological Activity of Chemically Immobilized rhBMP-2 on Titanium surfaces in vivo," *Mat.-wiss u. Werkstoffiech.*, vol. 32, pp. 942-948, 2001.

Unverdorben et al., "Comparisons of a Silicon Carbide Coated Stent versus a Noncoated Stent in Humans: The Tenax™-versus Nir™-Stent Study (TENISS)," *Journal of Interventional Cardiology*, vol. 16, No. 4, pp. 325-333.

Tsui et al., "Plasma sprayed hydroxyapatite coatings on titanium substrates, Part 2: optimisation of coating properties," *Biomaterials*, vol. 19, pp. 2031-2043, 1998.

Storm et al., "GDF5 Coordinates Bone and Joint Formation during Digit Development," *Developmental Biology*, vol. 209, pp. 11-27, 1999.

Schnaar et al., "Adhesion of Chicken Hepatocytes to Polyacrylamide Gels Derivatized with *N*-Acetylglucosamine," *The Journal of Biological Chemistry*, vol. 253, No. 21, pp. 7940-7951, 1978.

Schmitt et al., "Bone Morphogenetic Proteins: An Update on Basic Biology and Clinical Research," *Journal of Orthopaedic Research*, vol. 17, pp. 269-278, 1999.

Sampath et al., "Bovine Osteogenic Protein Is Composed of Dimers of OP-1 and BMP-2A, Two Members of the Transforming Growth Factor-β Superfamily," *The Journal of Biological Chemistry*, vol. 265, No. 22, pp. 13198-13205, 1990.

Padgett et al., "A transcript from a *Drosophila* pattern gene predicts a protein homologous to the transforming growth factor-β family," *Nature*, vol. 325, pp. 81-84, 1987.

Özkaynak et al., Osteogenic Protein-2: A New Member of the Transforming Growth Factor-β superfamily expressed early in embryogenesis,: *The Journal of Biological Chemistry*, vol. 267, No. 35, pp. 25220-25227, 1992.

Massagué, "The Transforming Growth Factor-β Family," *Annu. Rev. Cell Biol.*, vol. 6, pp. 597-641, 1990.

Lyons et al., "*Vgr-1*, a mammalian gene related to *Xenopus Vg-1*, is a member of the transforming growth factor β gene superfamily," *Proc. Natl. Acad. Sci. USA*, vol. 86, pp. 4554-4558, 1989.

Lind, "Growth factors: Possible new clinical tools: a Review," *Acta Orthop Scand*, vol. 67, No. 4, pp. 407-417, 1996.

Özkaynak et al., "OP-1 cDNA encodes an osteogenic protein in the TGF-β family," *The EMBO Journal*, vol. 9, No. 7, pp. 2085-2093, 1990.

Özbek et al., "Coronary Implantation of Silicone-Carbide-Coated Palmaz-Schatz Stents in Patients With High Risk of Stent Thrombosis Without Oral Anticoagulation," *Catheterization and Cardiovascular Diagnosis*, vol. 41, pp. 71-78, 1997.

Nishitoh et al., "Identification of Type I and Type II Serine/Threonine Kinase Receptors for Growth/Differentiation Factor-5," *The Journal of Biological Chemistry*, vol. 271, No. 35, pp. 21345-21352, 1996.

Lichtinger et al., "Osseointegration of Titanium Implants by Addition of Recombinant Bone Morphogenetic Protein 2 (rhBMP-2)," *Mat. wiss. u.Werkstoffiech.*, vol. 32, pp. 937-941, 2001.

Li et al., "Mineral Dusts Oxidize Methionine Residues: Probable Mechanism of Inactivation of Alpha-1-Antitrypsin," *Ann. occup. Hyg.*, vol. 41, Supplement 1, pp. 379-383, 1997.

Katagiri et al., "The Non-Osteogenic Mouse Pluripotent Cell Line, C3H10T1/2, is Induced to Differentiate Into Osteoblastic Cells by Recombinant Human Bone Morphogenetic Protein-2," *Biochemical and Biophysical Research Communications*, vol. 172, No. 1, pp. 295-299, 1990.

Jennissen, "Ultra-hydrophile metallische Biomaterialien," vol. 2, No. 1, pp. 45-53, 2001.

Hofma et al., "Recent Developments in Coated Stents," *Current Interventional Cardiology Reports*, vol. 3, pp. 26-28, 2001.

Endo, "Chemical Modification of Metallic Implant Surfaces with Biofunctional Proteins (Part 1) Molecular Structure and Biological Activity of a Modified NiTi Alloy Surface," *Dental Materials Journal*, vol. 14, No. 2, pp. 185-198, 1995.

Brown, "Incomplete Labeling of Pharmaceuticals: A List of "Inactive" Ingredients," *The New England Journal of Medicine*, vol. 309, No. 7, p. 439, 1982.

Celeste et al., "Identification of transforming growth factor β family members present in bone-inductive protein purified from bovine bone," *Proc. Natl. Acad. Sci.*, USA, vol. 87, pp. 9843-9847, 1990.

Albrektsson, "Hard tissue response," *Handbook of Biomaterial Properties*, Chapter 3, pp. 500-512, 1998.

Blackburn et al., "Carbohydrate-specific Cell Adhesion Is Mediated by Immobilized Glycolipids," *The Journal of Biological Chemistry*, vol. 258, No. 2, pp. 1180-1188, 1983.

American Academy of Pediatrics, Committee on Drugs, "Inactive Ingredients in Pharmaceutical Products," *Pediatrics*, vol. 76, No. 4, pp. 635-643, 1985.

International Conference on Harmonization, Topic Q3C, Impurities: Residual Solvents, www.emea.eu.int, Mar. 1998.

International Search Report and Written Opinion of International Application No. PCT/EP2005/002506, filed Mar. 3, 2005, both mailed Sep. 14, 2005.

Office Action issued in Japan, Patent Application No. 2007-502290, dispatch date Jun. 8, 2010, 3 pgs.

* cited by examiner

COATED IMPLANTS, THEIR MANUFACTURING AND USE THEREOF

The present invention relates to a method of coating of a device, preferably implants, with a substance comprising the steps of (a) contacting said device with a solution of said substance or substrate, and (b) drying said device while being in contact with said solution. The present invention also relates to a packaging container for a device, preferably an implant, said packaging container being adapted such that said device is coatable within said packaging container. Moreover, the present invention uses the well known method of coating the inner surfaces of a packaging container for a device, preferably implants, to achieve the directed deposition of the substance onto the implant, comprising the steps of (a) siliconizing said inner surfaces of said container using a silicone emulsion, and (b) heat-curing to form a baked-in silicone layer on said inner surfaces of said container. Furthermore, the present invention encompasses a coated device, preferably an implant, obtainable by a method according to the present invention. The present invention also relates to the use of said method of coating devices for improving the homogeneous distribution of the coating on the device. Finally, the present invention relates to the use of said method of coating in a designed packaging container for improving and/or controlling the deposition of the substance to be coated on said device between said container and said device.

During the last decades, many methods were described to improve the quality of implants concerning their biocompatibility and interaction with the surrounding tissue. The demands for implants are extreme (e.g. for bone implants, because such devices have to be rigidly fixed to the bone and be stable to e.g. high pressure (e.g. teeth, joints). Another application of coated implants is drug eluting stents to surpass the restenosis of coronary or other arteries. The initial tissue response after implantation is dependent on the presence of specific growth factors released from the surrounding tissues that stimulate cell growth and differentiation to enhance the incorporation and modulation of cell growth.

Although there are well-established fixation methods for dental implants there is still a tendency for them to loosen with time. A variety of approaches have been described in order to improve the incorporation of the respective implant (osseointegration). These approaches include the coating of implants of different sources (e.g. ceramic, metal or others, see EP-B1-0 657 146) with biodegradable materials (e.g. tri-calcium phosphate, hydroxyl apatite, carbonated apatite, calcium deficient hydroxyl apatite) and various methods for pre-treating device surface (e.g. the etching of metal surfaces; see EP-A-0 389 713, WO 95/13101, EP-A-1 251 889). Surface irregularities in the nanometer and micrometer range are assumed to improve the collagen and cell ingrowth (T. Albrektsson in: Handbook of Biomaterials (Black, J and Hastings, G (eds.), Chapman & Hall, London, 1998, pp 500-512).

Coating of metal implants with ceramic surfaces is described as e.g. the mixture of two powders, one metal powder and one powder containing calcium phosphate (EP-A-0 467 948) processed to implant material during a sintering process.

A variety of other sintering methods are described to manufacture composite ceramic material (DE-A-29 28 007, U.S. Pat. No. 4,882,196, EP 1251889). A main focus is laid on the coating of metal surfaces with calcium phosphates like tri-calcium phosphate or hydroxyapatite (Y. Tsui et al. (1998), Plasma sprayed hydroxyapatite coatings on titanium substrates, Biomaterials, 19: 2031-43, 19: 2015-29), which allow an improved incorporation of the implants (U.S. Pat. No. 6,312,472; US-A-2002/0038149). The described calcium phosphates and a variety of other inorganic biocompatible materials have the characteristic to form pores. These pores are said to enhance the incorporation of the implant into the native bone (WO 00/72776; U.S. Pat. No. 4,051,598; EP-A-0 806 211, Jennissen, H. et al. (2001), Biomaterialien, 2: 45-53) as the native bone is growing into the pores at the same time biodegrading the inorganic calcium phosphate layer of the implant (WO 96/10370; WO 01/97679). Besides the composite material implants are described consisting of layers, where the lower layer of the implant, often comprising metal or alloys like titan or titan alloy (WO 98/43550; WO 00/72777) is coated with a layer of the calcium phosphates (EP-A-0 478 532). Typically the coating with calcium phosphates is achieved by hydrothermal treatment (EP-A-0 548 365) or by soaking and precipitation (U.S. Pat. No. 6,129,928; WO 97/41273) or plasma spraying (U.S. Pat. No. 5,697,997; U.S. Pat. No. 6,113,993; EP-A-0 548 365, EP-A-0 739 191; Lichtinger, T. K. et al. (2001), Mat.-wiss. u. Werkstofftech, 32: 937-941).

The layer of calcium phosphate on the main body of the implant can be part of either a mixture of materials within one layer (WO 98/48862; U.S. Pat. No. 5,934,287; US-A-2002/0033548) or a multilayer formation (WO 02/09788; U.S. Pat. No. 6,322,728).

Besides to the modifications of the surface several methods are described in which proteins or protein mixtures (mainly growth factors) are coated onto orthopaedic or dental implants. These proteins are said to significantly accelerate the incorporation of implants (Lichtinger, T. K. et al. (2001), Mat.-wiss. u. Werkstofftech, 32: 937-941; Shah, A. et al. (1999), Biology of the cell 91: 131-142). Several methods are described for the direct coating of proteins onto the metal surfaces. However, these methods have several disadvantages, especially the rapid release of proteins from the metal surface, which does not allow maintaining of the protein for the time interval necessary for the induction of bone formation (Lichtinger, T. K. et al. (2001), Mat.-wiss. u. Werkstofflech, 32: 937-941).

In order to avoid the initial rapid release (spontaneous burst) of the protein Endo (Endo K. et al. (1995), Dental Materials Journal 14: 185-198) and Voggenreiter (Voggenreiter G et al. (2001), Materialwiss. Werkstofftech. 32: 942-948) describe the immobilization of the proteins by covalent binding to the metal surface. The activity of the respective proteins is maintained. However, the covalent binding may induce structural changes, which have impact on the activity and immunogenicity of proteins.

Many researchers have stated that successful implantation of the osteogenic factors for endochondral bone formation requires that the proteins are associated with a suitable carrier material or matrix which maintains the proteins at the site of application (U.S. Pat. No. 5,344,654). In order to overcome these difficulties U.S. Pat. No. 5,258,029 teaches "the osteogenic protein of the invention will normally be formulated in osteogenically effective amounts with pharmaceutically acceptable solid or fluid carriers. Preferably, the formulations include a matrix that is capable of providing a structure for developing bone and cartilage. Potential matrices may be biodegradable or non-biodegradable, and may be chemically or biologically defined. The suspension of the TGF-β-protein and the carrier is dried and subsequently applied to the load carrying prosthetic. Disadvantages of these methods are the use of animal derived collagens or inorganic components, which may be abraded during implantation.

A further method to overcome the quick outwash of the protein is described by Lichtinger et al. (2001), loc. cit. who treat the titan alloy surface with chromosulfuric acid in order to achieve an ultrahydrophilic bioadhesive surfaces. However, chromosulfuric acid should be avoided during the manufacture of medicinal products or medical devices as residual amounts of such acid remaining on the surface may cause oxidation of the protein with subsequent structural and functional changes and also may cause harm to the patient (Material safety data sheet Cr (VI)).

Further methods are described in WO 00/72777 and WO 00/72778 which use a depot which is formed by a pore arrangement of a thick oxide layer on the titanium surface or by internal spaces, channels or recesses. However, it is well known that proteins tend to become oxidized in the presence of metals and metal ions (Li et al. (1997), especially transition elements with catalytical activity in contact with oxygen in the absence of any protecting substances, Ann. Occup. Hyg. 41, suppl. 1, 379-383). Thus, a drawback of the aforementioned devices may be that the proteins are oxidized on the surfaces of the implants. The oxidation may result in structural changes, which can result in the formation of immunogenic reactions and loss of activity.

Another drawback of so far known coated devices is that they are not homogenously coated with a bioactive substance, which renders such devices only insufficiently suitable for, e.g. implantation. There are several reasons why devices may suffer from such disadvantages. For example, the coated substance being a protein is degraded or oxidized during the coating process and/or precipitates to insoluble aggregates or is present in insufficient amounts. Accordingly, the coating does not exert the desired biological effect, e.g. induction of bone growth or attraction of potential bone forming cells. In addition, coating solutions of the prior art also often contains toxic ingredients, e.g. organic solvents, which are used for solubilizing the substance, which should be coated on an implant. Yet, toxic substances are of course not desired on medical implants (EMEA, ICH Topic Q 3 C, Impurities: Residual Solvents). So far devices, e.g. metal implants are mainly coated manually with a coating solution, which is a labour intensive process and hardly applicable under GMP-conditions. However, the demand for coated devices for use as implants in various fields of medical applications has dramatically increased. Hence, there is also a need for the cost efficient coating of aseptic devices particularly with regards to producibility in large-scale amounts having GMP-quality.

Accordingly, the technical problem underlying the present invention is to provide an improved method for coating a device, preferably an implant, with a substance, and to provide a container for use in said method. The objective is to ensure a cost effective method, to deposit the substance quantitatively and homogenous onto the device. This encompasses the commercial realization, especially in pharmaceutically acceptable and state of the art aseptic processing. This problem is solved with the features of the claims.

According to a first aspect, the present invention provides a method of coating of a device with a substance comprising the steps of: (a) contacting said device with a solution of said substance or substrate in a container, and (b) drying said device while being in contact with said solution. According to the invention the container fulfils both properties as coating vessel and primary packaging container for the coated device. When used in the context of the present invention, the terms "substance" and "substrate" are interchangeable used.

The method preferably comprises the step of removing volatile components from said solution of said substance or substrate, wherein said removal step is performed before, simultaneously or after step (b). This removal of volatile components influences, particularly shifts e.g. the pH-value of the solution to control the solubility of the substance to a desired value.

The substance is preferably a pharmaceutically active substance such as a protein or peptide, a polysaccharide (Schnaar et al., 1978, Adhesion of hepatocytes to polyacrylamide gels derivitized with N-acetylglucosamine, J. Biol. Chem. 253, 7940-7951), a glycolipide (Blackbourn and Schnaar, (1983) J. Biol. Chem., 258(2), 1180-1188) or a peptide or a small molecule. The terms "protein" or "peptide" are used interchangeable in the context of the present invention.

An example for a protein is a dissolved osteoinductive protein, preferably a member of the TGF-β-superfamily. Within the scope of said pharmaceutically active substance are combinations of one or more proteins, peptides or small molecules as described infra. Also combinations of proteins, peptides or small molecules are envisaged.

The TGF-β family of growth and differentiation factors has been shown to be involved in numerous biological processes comprising bone formation. All members of said family are secreted peptides comprising a characteristic domain structure. On the very N-terminus, the TGF-β family members comprise a signal peptide or secretion leader. This sequence is followed at the C-terminus by the prodomain and by the sequence of the mature peptide. The sequence of the mature peptide comprises seven conserved cysteins, six of which are required for the formation of intramolecular disulfide bonds whereas one is required for dimerization of two peptides. The biologically active TGF-β family member is a dimer, preferably composed of two mature peptides. The TGF-β family members are usually secreted as proproteins comprising in addition to the mature sequence the prodomain. The prodomains are extracellularly cleaved off and are not part of the signalling molecule. It has been reported, however, that the prodomain(s) may be required for extracellular stabilization of the mature peptides. In the context of the present invention, the term "TGF-β family member" or the proteins of said family referred to below encompass all biologically active variants of the said proteins or members and all variants as well as their inactive precursors. Thus, proteins comprising merely the mature sequence as well as proteins comprising the mature protein and the prodomain or the mature protein, the prodomain and the leader sequence are within the scope of the invention as well as biologically active fragments thereof. Whether a fragment of a TGF-β member has the biological activity can be easily determined by biological assays described, e.g. in: Katagiri et al. (1990) Biochem. Biophys. Res. Commun. 172: 295-299 or Nishitoh et al. (1996) J. Biol. Chem. 271: 21345-21352.

Preferably, the biological activity according to the invention can be determined by in vivo models as described in WO 03/043673. Furthermore, encompassed by the present invention are variants of the TGF-β members which have an amino acid sequences being at least 75%, at least 80%, at least 90%, at least 95%, at least 96%, at least 97%, at least 98% or at least 99% identical to the amino acid sequences of the members of the TGF-β family.

An overview of the members of the TGF-β superfamily is given in: Wozney J M, Rosen V (1998) Olin Orthop 346: 26-37. The amino acid sequences of the members of the TGF-β family can be obtained from the well-known databases such as Swiss-Prot via the Internet (http://www.expasy.ch/sprot/sprot-top.html).

More preferably, said member of the TGF-β family is a member of the BMP subfamily. The members of the Bone Morphogenetic Protein (BMP) subfamily have been shown to be involved, inter alia, in the induction and re-modelling of bone tissue. BMPs were originally isolated from bone matrix. These proteins are characterized by their ability to induce new bone formation at ectopic sites. Various in vivo studies demonstrated the promotion of osteogenesis and chondrogenesis of precursor cells by BMPs and raise the possibility that each BMP molecule has distinct role during the skeletal development. More details about the molecular and biological properties of the BMPs are described in: Wozney J M, Rosen V (1998) loc. cit., Schmitt et al. (1999), J Orthop Res 17: 269-278 and Lind (1996), Acta Orthop Scand 67: 407-17.

Members of the morphogen family of proteins include the mammalian osteogenic protein-1 (OP-1, also known as BMP-7, and the Drosophila homolog 60A), osteogenic protein-2 (OP-2, also known as BMP-8), osteogenic protein-3 (OP-3), BMP-2 (also known as BMP-2A or CBMP-2A, and the Drosophila homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF-3 (also known as Vgr2), GDF-8, GDF-9, GDF-10, GDF-11, GDF-12, BMP-13, BMP-14, BMP-15, GDF-5 (also known as CDMP-1 or MP52), GDF-6 (also known as CDMP-2), GDF-7 (also known as CDMP-3), the Xenopus homolog VgI and NODAL, UNIVIN, SCREW, ADMP, and NEURAL. Members of this family encode secreted peptide chains sharing common structural features, including processing from a precursor "pro-form" to yield a mature peptide chain competent to dimerize and containing a carboxy terminal active domain, of approximately 97-106 amino acids. All members share a conserved pattern of cysteines in this domain and the active form of these proteins can be either a disulfide-bonded homodimer of a single family member or a heterodimer of two different members (see, e.g. Massague (1990), Annu. Rev. Cell Biol. 6: 597; Sampath et al. (1990), J. Biol. Chem. 265: 13198). See also, U.S. Pat. No. 5,011,691; U.S. Pat. No. 5,266,683, Ozkaynak et al. (1990), EMBO J. 9: 2085-2093, Wharton et al. (1991), PNAS 88:9214-9218), (Ozkaynak (1992), J. Biol. Chem. 267: 25220-25227 and U.S. Pat. No. 5,266,683); (Celeste et al. (1991), PNAS 87:9843-9847); (Lyons et al. (1989), PNAS 86:4554-4558). These disclosures describe the amino acid and DNA sequences, as well as the chemical and physical characteristics, of these osteogenic proteins. See also, Wozney et al. (1988), Science 242:1528-1534; BMP 9 (WO93/00432); DPP (Padgett et al. (1987), Nature 325:81-84; and Vg-1 (Weeks (1987) Cell 51: 861-867).

Preferably, said member of the BMP family is BMP-1, BMP-3, BMP-4, BMP-5, BMP-6, BMP-8, BMP-9, BMP-10, BMP-11, BMP-12, BMP-13, BMP-14, BMP-14 or BMP-16. Most preferably, said member of the BMP family is BMP-2 or BMP-7.

The amino acid sequence for the preform of BMP-2 is deposited under Swiss-Prot Accession number P12643 (Genebank Accession number GI: 115068). Amino acids 1 to 23 correspond to the signal sequence, amino acids 24 to 282 correspond to the propeptide and amino acids 283 to 396 correspond to the mature protein. The amino acid sequence for the preform of BMP-7 is deposited under Swiss-Prot Accession number P18075 (Genebank Accession number GI: 115078). Preferably, BMP-2 or BMP-7 refers to the preform, to the proform or to the mature BMP-2 or BMP-7 peptide, respectively. Moreover also encompassed are fragments of said proteins having essentially the same biological activity, preferably osteoinductive properties. More sequence information for BMP-2 and BMP-7 is provided below. Also more preferably, said member of the TGF-β family is a GDF. Growth and Differentiation Factor (GDF) have been also shown to be involved, inter alia, in the induction and re-modelling of bone tissue. Growth Differentiation Factor 5 (GDF-5), also known as cartilage-derived morphogenetic protein 1 (CDMP-1) is a member of subgroup of the BMP family, which also includes other related proteins, preferably, GDF-6 and GDF-7. The mature form of the protein is a 27 kDa homodimer. Various in vivo and in vitro studies demonstrate the role of GDP-5 during the formation of different morphological features in the mammalian skeleton. Mutations of GDF-5 are responsible for skeletal abnormalities including decrease of the length of long bones of limbs, abnormal joint development in the limb and sternum (Storm & Kingsley (1999), Development Biology, 209, 11-27). The amino acid sequence between mouse and human is highly conserved.

Preferably, said member of the GDF subfamily is GDF-1, GDF-3, GDF-6, GDF-7, GDF-8, GDF-9, GDF-10 or GDF-11.

Most preferably, said member of the GDF subfamily is GDF-5. The amino acid sequence for the preproform of GDF-5 is deposited under Swiss-Prot Accession number P 43026 (Genebank Accession number GI: 20141384). Preferably, GDF-5 refers to the preproform, to the proform or to the mature GDF-5 peptide. Moreover also encompassed are fragments of GDF-5 having essentially the same biological activity, preferably osteoinductive properties.

Further examples of TGF-β family members which are envisaged to be coated on a device of the present invention are described, for example, in EP-B1 0 372 031, EP-A2 0 723 013, EP-A2 1 221 484, EP-B1 0 362 367, EP-A2, 1 225 225, EP-B1 0 714 665, EP-A10 646 022, EP-B1 0 584 283, EP-B1 0 448 704, EP-B1 0 643 767, EP-B1 0 812 207, EP-A11 220 693, EP-A11 223 990, EP-A11 150 725, EP-B1 0 679 097, EP-B1 0 601 106, EP-A2 0 601 135, EP-A10 972 520 or EP-B1 0 575 555.

Still other useful proteins include proteins encoded by DNAs competent to hybridize to a DNA encoding an osteogenic protein as described herein, and related analogs, homologs, muteins (biosynthetic variants) and the like. Publications disclosing such DNA sequences, as well as their chemical and physical properties, include: OP-1 and OP-2: U.S. Pat. No. 5,011,691, U.S. Pat. No. 5,266,683, Ozkaynak et al. (1990), EMBO J. 9: 2085-2093; OP-3: WO94/10203 (PCT US93/10520); BMP-2, BMP-3, BMP-4: WO88/00205, Wozney et al. (1988), Science 242:1528-1534); BMP-5 and BMP-6: Celeste et al. (1991), PNAS 87: 9843-9847; Vgr-1: Lyons et al. (1989), PNAS 86: 4554-4558; DPP: Padgett et al. (1987), Nature 325: 81-84; Vg-1: Weeks (1987), Cell 51: 861-867; BMP-9: WO95/33830 (PCT/US95/07084); BMP-10: WO94/26893 (PCT/US94/05290); BMP-11: WO94/26892 (PCT/US94/05288); BMP-12: WO95/16035 (PCT/US94/14030); BMP-13: WO95/16035 (PCT/US94/14030); GDF-1: WO92/00382 (PCT/US91/04096) and Lee et al. (1991), PNAS 88: 4250-4254; GDF-8: WO94/21681 (PCT/US94/03019); GDF-9: WO94/15966 (PCT/US94/00685); GDF-10: WO95/10539 (PCT/US94/11440); GDF-11: WO96/01845 (PCT/US95/08543); BMP-15: WO96/36710 (PCT/US96/06540); MP121: WO96/01316 (PCT/EP95/02552); GDF-5 (CDMP-1, MP52): WO94/15949 (PCT/US94/00657) and WO96/14335 (PCT/US94/12814) and WO93/16099 (PCT/EP93/00350); GDF-6 (CDMP-2, BMP-13): WO95/01801 (PCT/US94/07762) and WO96/14335 and WO95/10635 (PCT/US94/14030); GDF-7 (CDMP-3, BMP-12): WO95/10802 (PCT/US94/07799) and WO95/10635 (PCT/US94/14030). In another embodiment, useful proteins include biologically active biosynthetic constructs, including novel biosynthetic morphogenic proteins and chimeric proteins designed using sequences from two or more known morphogens. See also the biosynthetic constructs disclosed in U.S. Pat. No. 5,011,691 (e.g. COP-1, COP-3, COP-4, COP-5, COP-7, and COP-16).

In the context of the present invention a peptide or small molecule, which has the biological activity of a protein being a member of the TGF-β family is preferred. More preferably, the peptide or small molecule has osteoinductive and/or osteogenic properties. These properties can be determined by methods as described herein or in WO 03/043673. The term "osteoinductive" refers to the capability of the transformation of mesenchymal stem cells and pre-osteoblasts into osteoblasts. A prerequisite for osteoinduction is a signal, which is distributed by the device into the surrounding tissues where the aforementioned osteoblast precursors and other mesenchymal cells become activated. Osteoinduction as used herein encompasses the differentiation of mesenchymal cells into the bone precursor cells, the osteoblasts. Moreover, osteoinduction also comprises the differentiation of said osteoblasts into osteocytes, the mature cells of the bone. Thus, osteoinduction requires differentiation of undifferentiated or less-differentiated cells into osteocytes, which are capable of forming the bone. As has been described above, the osteoinductive proteins used in accordance with the present invention are slowly released from the device after implantation and are distributed efficiently in the surrounding tissues. Moreover, the proteins and peptides encompassed by the present invention have osteoinductive properties in vivo. For example, it is well known in the art that the Transforming Growth Factor-β (TGF-β) superfamily encompasses members, which have osteoinductive properties. Individual members of said TGF-β superfamily which have particular well osteoinductive properties are listed supra and infra and described herein. In conclusion, the osteoinductive proteins of the device of the present invention on the surface and after having been released from the carrier will serve as a osteoinductive signal for the osteocyte precursors of the tissue surrounding the side of implantation of the device.

The term "osteogenic" describes the synthesis of new bone by osteoblasts. In accordance with the present invention, pre-existing bone in the surrounding of the side of implantation of the device grows into the device using the structure of the device as a matrix onto which the osteocytes can adhere.

Preferred examples of pharmaceutically active substances are peptides such as interleukins, EGF, PDGF, IGF, FGF, TGF-alpha, TGF-beta, Hirudin, tissue plasminogen activator and variants, parathormone. A "variant" or "derivative" of any of the aforementioned pharmaceutically active substances is to be understood to have the same activity or effect as the unmodified drug substance.

Preferred examples of a polysaccharides, lipids or glycolipids or small molecule are heparin or heparin mimetic substances, taxanes e.g. paclitaxen, antibiotics, steroids or hormones or phosphorylcholine.

Another example of a substance with which a device, e.g. a stent or ocular lenses according to the present invention can be coated are organic coatings such as biogold. Biogold is a commercial polymer coating, consisting of short-chain hydrocarbons (U.S. Pat. No. 4,994,498 Biogold Cooperation). Another example of an inorganic coating substance that can be coated onto a device, e.g. a stent of the present invention is silicon-carbide (SiC), iridium oxide. (Ozbek (1997), Cathet. Cardiovasc Diagn 41: 71-78) or TENISS which can be obtained from Tenax, Biotronik GmbH, Berlin, Germany (Unverdorben M. (2000), J. of interventional cardiollogy 16(4): 325). SiC is a ceramic and consists of amorphous hydrogenated silicium carbide.

Yet, also synthetic polymers can be coated onto a device, e.g. a stent according to the present invention such as biocompatible or degradable polymers are preferably polylactic acid, cellulose, polyurethane polyester metacryloyl phosphorylcholine (PC) laurylmethacrylate or polytetrafluoroethylene (PTFE). Furthermore, polymers of natural origin are envisaged to be coated onto a device of the present invention, such as hyaluronic acid, chondroitin sulphate, chitosan, alginate or fibrin. As a non-limiting example of a protein that can be coated onto a device, e.g. stent of the present invention a glycoprotein IIb/IIIa antibody is to be named. Additionally, drugs such as taxanes (e.g. paclitaxel) are envisaged to be coated onto a device, e.g. stent of the present invention. For a review describing various, but non-limiting coatings of stents, see Sjoerd (2001), Curr. Intervent. Cardiol. Rep. 3: 28-36.

The pharmaceutically active substance described herein is in a preferred embodiment immobilized in an inorganic or organic bioresorbable matrix or material.

Alternatively, the substance comprises non-active ingredients. The term "active" when used in the context of the present invention is interchangeable with the term "inactive" and means any component of a drug product intended to furnish pharmacological activity or other direct effect in the diagnosis, cure, mitigation, treatment, or prevention of disease, or to affect the structure or any function of the body of humans or other animals. Inactive ingredients are, for example, described in Brown (1983), N Engl J. Med., 309: 439-441 or in American Academy of Pediatrics, Committee on Drugs "Inactive" ingredients in pharmaceutical products. Pediatrics (1985), 76: 635-643. A list of inactive ingredients is also available at the FDA. Such ingredients include methionine, saccharose or acetic acid It is also encompassed by the present invention that the substance comprises any kind of ceramics like calcium phosphates. The term "calcium phosphate" encompasses compositions comprising calcium ions, phosphate ions and, optionally, further ions or atoms which are suitable for the carrier of the present invention e.g. $CO_3^{2-}$, $F^-$, $OH^-$, $Mg^{2+}$. The calcium phosphates as used in accordance with the present invention are crystalline or amorphous having a three dimensional structure suitable for the device of the present invention as set forth above. A list of preferred and well-known calcium phosphates is given herein after. Said calcium phosphate is beta tricalcium phosphate, alpha tricalcium phosphate, hydroxyapatite, carbonated apatite or a calcium deficient hydroxyapatite or calcium phosphate containing cement.

Preferably, a device coated according to the methods of the present invention is homogenously coated in the area of interest with a substance described herein. Said substance is preferably in the form of a solution. Said solution can be composed by the person skilled in the art based on the solubility of, e.g. the osteoinductive protein which depends on the pH, the ionic strength and the influence of the carrier on said parameters after contacting the carrier with said solution. In accordance with the present invention it has been found that a suitable solution for the method of the present invention comprises only components, which do not influence the oxidation status of the osteoinductive protein.

The term "homogeneously coated" means that the surface of the carrier is entirely coated with said osteoinductive protein, whereby essential reproducible and defined amounts of protein are present onto the desired area of the surface of said carrier. A homogeneously coated carrier in accordance with this invention, preferably, exhibits a maximum covering with the osteoinductive protein on its surface. Homogenous coating is a prerequisite for efficient release and homogenous distribution and activity of the osteoinductive protein into the tissue surrounding the site of implantation. Moreover, it is to be understood that the osteoinductive proteins are not aggregated and partially or entirely inactivated due to precipitation or micro-precipitation, rather attachment of biologically active, non-aggregated proteins is to be achieved by homogenous coating. Said homogenous coating can be achieved by the method of the present invention and as described in the accompanied Examples. Further, means and methods for controlling homogeneous coating, quantification and characterization of the immobilized protein are described in WO 03/043673.

According to the present invention the protein or peptide is immobilized on the surface of the device. It is preferred that the binding of said protein or peptide to the carrier is reversible. Hence, it is envisaged that the protein or peptide, which has osteoinductive properties is not coupled to the (for example metallic) surface of the device by means of covalent bonding. Preferably, coupling occurs via electrostatic interactions, hydrophobic or non-electrostatic interactions, such as Van-der-Waals forces. Due to the reversible binding of the osteoinductive protein, dissolution of said protein is allowed once the device has been brought into a suitable in vivo surrounding, such as a bone cavity or an artery. Preferably, said dissolution of the proteins is slow release allowing diffusion of the protein into the tissue which surrounds the device. Thus, the device allows the local presence of native proteins, which accelerate the formation of e.g. new bone and the ingrowth of the bone into the surface of the matrix or coated stents inhibit the rapid restenoses.

Many methods are described for the stabilization of proteins in pharmaceutical products. However, the experiments underlying this invention demonstrated that the well-known techniques of protein stabilization in liquid or freeze-dried protein formulations can not be directly adapted to the adsorbed protein onto a metal surface. The coating of proteins onto ceramic or metal surfaces e.g. titan or titan alloys according to the methods disclosed in the state of the art referred to supra cause the occurrence of modified species of the protein which result in aggregation or oxidation of the proteins (for details see Example 6). Moreover, even the addition of reducing agents does not decrease the amount of oxidized protein. Thanks to the method of the present invention it is possible to manufacture devices, which after implantation will efficiently augment bone. Advantageously, the undesirable side effects, such as inflammation due to the enhanced immunogenicity of oxidized proteins, can be avoided. Moreover, the method of the present invention will allow a less time consuming and more cost effective manufacturing process for the medical devices of the present invention because coating of the metal or alloy corpus of the implant and packaging can be made in a one step procedure as described herein. In addition, said one step procedure assures conservation of the activity of the substance coated on the device or implant due to fast drying at low temperature as described herein and the absence of oxygen during the coating process as well as in the packaging container. Another advantage is that the coating and packaging process allows quantity production, whereby the production complies with GMP-standards for aseptic processing instead of other application techniques for the coating solution by dipping, dropping or spraying. Accordingly, implants coated according to the methods described herein have the desired aseptic high quality for medical applications, especially parenteralia.

The device of the invention may be an implant, which means that the terms "device" and "implant" as used herein are interchangeable. It is well-known that the term "implant" refers to every device as provided by the instant invention which is designed to be brought totally or partially underneath the epithelial surface (Koeck, B. and Wagner, W. (Eds.) 1996). The implant may be flat, dense or of a complex shape, i.e. any conventionally used or operable device can be used. The above-mentioned implants range from a simple cylindrical shape as used e.g. for replacement of long bones or as a basis for artificial teeth, to flat implants as used for replacement of cephalic flat bones and artificial joints like hip, knee or elbow. Further types of implants are biodegradable ceramic implants of structured (porous) three-dimensional shape (e.g. blocks or cylinders) from natural origin (bovine, human) or synthetic material (beta-TCP).

Preferably, the implant or device is an entity, which comprises at least two components. One of said components is a carrier. Carriers, which can be used within the meaning of the present invention include solid carriers, such as full metal or alloy carriers, and metal or alloy matrices. In addition the present invention encompasses solid carriers, which comprise hollow spaces and cavities. Moreover, said carrier, preferably, has an enlarged surface due to formation of macro- and micro-pores. Preferably, said macro- or micro-pores are restricted to the surface layer of the carrier. Also encompassed by the present invention are carriers, which consist of at least two different components, wherein a metal or alloy component is used as core or core layer and, e.g. a ceramic material is used as surface layer. This also encompasses the formation of implants or entire chirurgic prostheses. These prostheses are, preferably, formed from or coated with metallic surfaces as will be described in more detail below. Prostheses are made from titan or titan alloys or stainless steel.

Before contacting the solution comprising, for example, dissolved osteoinductive protein with a carrier containing a surface of metal or a metal alloy as described herein, it is envisaged that the respective metallic surface is preferably cleaned or treated to remove any surface contaminants like atmospheric gases (e.g. oxygen) or other hydrophobic contaminants to promote good adhesion strength of the coating. Several methods, which are suitable for this purpose, are well-known in the art and also exemplified in the appended examples. For example, the metallic surface of the devices of the invention may be rinsed with e.g. acetone, alkyl alcohols like ethanol and then heated to desorb volatile contaminants and afterwards rinsed with sterile distilled or demineralized water.

In another aspect of the present invention it is envisaged that the carrier of devices or implants are selected from the group consisting of synthetic organic materials, synthetic inorganic materials, organic materials of natural origin and inorganic materials of natural origin. Natural origin means compounds occurring in nature.

Preferably said synthetic organic materials are polyglycolid (PGA), polylactid (PLLA), poly-D/L-lactid (PDLLA), poly(glycolic-co-lactid acid) (PLGA), poly(3-hydroxybutyric acid) (P(3-HB), poly(3-hydroxy valeric acid) P(3-HV), poly(p-dioxanone) (PDS), poly(ε-caprolactone) (PCL), polyanhydride (PA), polyorthoester, polyethylene (PE), polypropylene (PP), polyethylenterephthalate (PET), polyglactine, polyamide (PA), polymethylmethacrylate (PMMA), polyhydroxymethylmethacrylate (PHEMA), polyvinylchloride (PVC), polyvinylalcohole (PVA), polytetrafluorethylene (PTFE), polyetheretherketone (PEEK), polysulfon (PSU), polyethylenglycole (PEG), polyvinylpyrolidone, polyurethane or polysiloxane. It is to be understood that any combination or copolymers of the aforementioned synthetic organic materials is also envisaged.

In another preferred embodiment, said synthetic inorganic materials are steel 316L, cobalt-chromium-alloy, titan, titan-alloy as described herein, gold, or platinum. It is to be understood that any combination of the aforementioned synthetic inorganic materials is also envisaged.

In a further preferred embodiment, said inorganic materials are β-tricalciumphosphate, α-tricalciumphosphate, hydroxylapatite, carbonated apatite, aluminium oxide, zirconium oxide, calcium carbonate, calcium sulfate or bioglass. It is to be understood that any combination of the aforementioned inorganic materials is also envisaged.

In still another preferred embodiment, said organic materials of natural origin are collagen, chitine, chitosane, hyaluronic acid, chondroitin sulphate, alginate, autologous bone, gelatine or fibrine. It is to be understood that any combination of the aforementioned organic materials of natural is also envisaged.

In another embodiment inorganic materials of natural origin are calcified bone or coralline derived material.

All organic or inorganic materials mentioned herein can also be used as carrier for the pharmaceutical active ingredient e.g. as encapsulation agent or transmitting/embedding to achieve drug immobilization, protecting and/or stabilization and/or controlled release. Preferable said pharmaceutically active substance can be immobilized in an inorganic or organic bioresorbable material.

The device or implant of the present invention, preferably, has an enlarged surface due to porous, beaded or meshed surface modifications. Such modifications can be introduced by methods well known in the art, including chemical or mechanical means. Moreover, it has been shown that the increased surface having irregularities in the nanometer and micrometer range are beneficial for osseointegration.

The term "osseointegration" when used herein means that bone has the ability to form new bone around the implant and to integrate with the implant. Integration means the attachment of bone cells to the implant surface resulting in a firm and permanent anchorage of the prosthetic reconstruction under functional load without pain, inflammation or loosening. It is envisaged that osseointegration is accompanied by new bone formation is to be carried out for treatment of traumatic, malignant or artificial defects, for the treatment of dental defects or for the treatment of hip, elbow, spine, knee, finger or ankle joint or bone defect filling material. The symptoms of the diseases and disorders referred to hereinabove are described in detail in standard text books of medicine, such as Pschyrembel and Stedman.

"New bone formation" means formation of endochondral bone or formation of intramembranous bone. In humans, bone formation begins during the first 6-8 weeks of fetal development. Progenitor stem cells of mesenchymal origin migrate to predetermined sites, where they either: (a) condense, proliferate, and differentiate into bone-forming cells (osteoblasts), a process observed in the skull and referred to as "intramembranous bone formation;" or, (b) condense, proliferate and differentiate into cartilage-forming cells (chondroblasts) as intermediates, which are subsequently replaced with bone-forming cells. More specifically, mesenchymal stem cells differentiate into chondrocytes. The chondrocytes then become calcified, undergo hypertrophy and are replaced by newly formed bone made by differentiated osteoblasts, which now are present at the site. Subsequently, the mineralized bone is extensively remodeled, thereafter becoming occupied by an ossicle filled with functional bone-marrow elements. This process is observed in long bones and referred to as "endochondral bone formation." In postfetal life, bone has the capacity to repair itself upon injury by mimicking the cellular process of embryonic endochondral bone development. That is, mesenchymal progenitor stem cells from the bone-marrow, periosteum, and muscle can be induced to migrate to the defect site and begin the cascade of events described above. There, they accumulate, proliferate, and differentiate into cartilage, which is subsequently replaced with newly formed bone.

Also within the scope of the present invention is a method for treating one or more of the diseases referred to in accordance with the uses of the present invention, wherein said method comprises at least the step of administering the device of the invention or a device which can be obtained by the method of the invention in a pharmaceutically acceptable form to a subject. Preferably, said subject is a human.

The device or implant may, moreover, comprise additional excipients. These excipients serve to stabilization or preservation of the protein, e.g. saccharides, amino acids, polyols or detergents or maintenance of the pH, e.g. buffer substances. Other preferred excipients encompassed by this invention include starch or modified starch, glucose, lactose, sucrose, gelatin, malt, rice, flour, chalk, silica gel, sodium stearate, glycerol monostearate, talc, sodium chloride, dried skim milk, glycerol, natural oils (e.g. castor oil), polethylen glycol, polypropylene glycolpropylene, glycol, water, ethanol and the like.

The term "saccharides" encompasses mono-, di- and polysaccharides. The structure and composition of mono-, di, and polysaccharides are well known in the art and are described in standard textbooks, such as Römpp, lexicon of chemistry. More preferably, said saccharide is a disaccharide. Most preferably, said disaccharide is sucrose or trehalose.

In another preferred embodiment of the device or the method of the invention said device is free of toxic substances.

The term "toxic substances", preferably, encompasses those toxic organic solvents and additives which are used by the methods described in the art, e.g. actetonitrile. Said substances may cause inflammation and other reactions after implantation of devices containing said substances. Said devices are therapeutically less acceptable due to said undesirable side effects which can not be avoided by the coating methods described in the art. Moreover, the international guidance for the development of therapeutic proteins require that in the manufacturing process harmful and toxic substances should be avoided (for details see: International Conference on Harmonization (ICH), Topic Q3C; www.emea.e-u.int/). However, the device of the present invention or a device which is obtainable by the method of the present invention is, advantageously, free or minimized of said toxic substances and, therefore, therapeutically well acceptable and fulfils the requirements of the regulatory authorities.

Moreover, in a further preferred embodiment of the implant or the method of the invention said device is free of infectious material.

Besides toxic substances, infectious material comprised by the implant may cause severe infections in a subject into which the device has been transplanted. Potentially infectious gelatin derived from bovine or porcine bones is, however, used as a protecting protein in many state of the art methods (M. Lind (1996), Acta Orthop Scand 67: 407-17).

The coating of the device of the invention with, for example, an osteoinductive protein is intended to initiate and stimulate the transformation of mesenchymal stem cells into osteoblasts and chondrocytes. Accordingly it is envisaged that only those parts of the device of the invention need to be coated, which are directed towards the respective bone tissue. Said part is preferably the entire surface or at least the parts thereof which are juxtaposed to the bone tissue. For example, a dental implant, which is used to replace a missing tooth, comprises a threaded part which is screwed into the jaw bone and an extended part (socket) which is used for anchoring an artificial tooth crown. Accordingly, it is only necessary to coat the threaded part with the osteoinductive protein. However, the part which is not coated with the osteoinductive protein may be coated with other agents which, such as calcium phosphates, collagen or similar agents.

The term "osteoinductive protein" or as set forth above, refers to Transforming Growth Factor-β (TGF-β) superfamily members which have osteoinductive properties, such as Growth and Differentiation Factor-5 or the proteins described herein or in the EP-patent applications or EP-patents mentioned supra. An important precondition for such an adsorption process of to the metallic surface is a sufficient solubility of the proteins in the coating solution as is described in WO 03/043673.

The drying step used in the method according to the first aspect of the present invention preferably isothermal drying is used as described in the following. Drying may also be achieved by vacuum- or freeze-drying. The term "drying" encompasses means for removing liquids. (Details about freeze-drying can be taken from "Good Pharmaceutical Freeze-Drying Practice", edited by Peter Cameron, interpharm Press, Inc., Buffalo Grove, Ill., USA).

The term "isothermal drying" refers to a drying method where the solvent is removed by evaporation of the solvent from the liquid phase to the gaseous phase and subsequently condensed at an ice-condenser. The ice-condenser is set to very low temperatures to reduce the saturated vapour pressure of the solvent to achieve a mass transport of the solvent out of the solution to the ice-condenser and to immobilize the solvent. Preferably the ice condenser is set to less than −50° C.

This process is carried out under reduced pressure (i.e. below standard atmospheric pressure) to enhance the evaporation of the solvent, while the temperature of the solution is hold at a defined temperature preferably by using a temperature regulated shelve where the product is located on.

The temperature is set by the equilibrium of evaporation and heating at a constant level to enhance the evaporation of the solvent and to prevent a freezing of the solution by lowering the temperature due to enthalpy of evaporation of the solvent and to protect the substrate from temperature induced degradation. Preferably the temperature is constant throughout the drying process.

Both, temperature and pressure are needed to be set carefully to ensure that the solution remains in the liquid state throughout drying. Preferably the drying process is carried out in a freeze-dryer to maintain and control the defined drying parameters during the drying process. Preferably the drying process is carried out in an oxygen free environment, e.g. by means of venting the drying chamber with Nitrogen, Argon etc.

Recently, coating of stents has become important to enhance hemocompatibility and tissue compatibility. Ongoing trials with new drug-eluting stents are believed to improve the treatment of restenosis and especially in-stent restenosis (see, e.g. the report "Recent Developments in Coated Stents), Hofma, Sjoerd H. et al. (2001), Current Interventional Cardiology Reports, 3: 28-36). The present invention also encompasses the coating of stents with the method according to the present invention. The coating of stents according to the present invention results in stents having a homogeneous coating over the entire surface of the stent, for example metallic stents (like Nitinol-stents) as is described herein.

According to the present invention, the coating of said device is performed while said device is contacted with the coating solution in its special adapted packaging container. In other words, according to the present invention, the containment for the device to be coated during the coating process is identical to the container used for packaging and storage the coated device, i.e. the same container is used for coating and subsequent packaging e.g. use in the large-scale production of single dose aseptic products, in particular for the use for pharmaceutical products.

Preferably, the solution containing the substance is an aqueous solution, most preferably an acidic solution. Of course, as is well known in the art, the pH of the solution containing the substance as well as excipients for adjusting the pH should be selected carefully.

For example, Ti-devices are preferably coated with protein by means of an aqueous solution of the protein applied to the metal surface and additional drying. This coating solution is formulated to provide sufficient stability for the protein during processing and storage. For example, rhGDF-5 is soluble in acidic solutions only. Thus, the pH value of the coating solution need to be set carefully to avoid acidic degradation of the protein on the one hand and precipitation at higher pH values on the other hand. Studies have identified a pH range of 3.0 to 3.5 as an ideal one (WO 03/043673). This pH should be constant during drying and must not shift to higher or lower values when the solution is concentrated during evaporation of the solvent. Experiments have shown, that a weak acid, for example, acetic acid is an ideal excipient for this purpose.

The term "weak acid" refers to organic or inorganic compounds containing at least one ionogenically bound hydrogen atom. Weak acids are well known in the art and are described in standard text books, such as Römpp, lexicon of chemistry. Preferably, said weak acids which have low dissociation degrees and are described by pK values between 3 and 7, preferred between 4 and 6.

As mentioned herein the solution in which the substance to be coated onto a device is an acidic aqueous solution. Preferably, the acidic aqueous solution contains HCl, acetic acid, citric acid and/or succinic acid.

In another preferred embodiment of the present invention the solution in which the substance to be coated onto a device is an organic solvent. Preferably, the organic solvent is glacial acetic acid, DSMO, anisole.

However, the present invention also contemplates that the solution in which the substance to be coated onto a device according to the methods of the present invention is solved in aliphatic or aromatic alcohols, ester, ethers, carbon hydrates, halogenated aliphatic or aromatic carbon hydrates and the like.

It is further preferred that the solution contains an antioxidant, like methionine or its derivatives (sulfite, ascorbic acid, glutatione) or radical scavenger as described in standard text books (Bauer, Frömming Führer, Lehrbuch der Pharmaceutischen Technologie, 6. Auflage, 1999). Examples are: Butylhydroxytoluol, butylhydroxyanisole, EDTA, mannitole, isopropanole, tocopherole, galuric acid esters.

The device to be coated is, for example, made of metal or metal alloy, preferably titanium or a titanium alloy or any one the materials described herein. It is preferred that the metals/metal alloys or other materials described herein of the invention are biocompatible. The term "biocompatible" means the quality of not having toxic or injurious effects on biological systems (Williams, D. F., (1988), Consensus and definitions in biomaterials, in Advances in Biomaterials, 8, de Putter, C., de Lange K., de Groot K., Lee A. J. C. (eds.), Elsevier Science Publishers B. V., Amsterdam). Said properties are known for titan or titan alloys. More preferably, the titan alloy is a titan alloy containing at least 50% titan. Furthermore preferably, said titan alloy is a Ti—Al—V-alloy, a Ti—Al—Fe alloy, a Ti—Al—Nb-alloy or a Ti—Mo—Zr—Al-alloy, Ti—Ni-alloy, most preferably Ti6Al4V.

The device to be coated with the method of the first aspect is preferably an implant or a stent, most preferably a dental implant or coronary stent.

In more detail, step (a) of the method of the first aspect of the present invention comprises the sub-steps of (a1) providing a packaging container for said device; (a2) filling said coating solution into said container; and (a3) inserting said device into said pre-filled container. The order of steps (a2) and (a3) can be reversed so that first the device is inserted into the container, and subsequently the coating solution. More preferably the method further comprises the step of applying a reduced pressure below atmosphere to ensure a complete wetting of the surface of interest, e.g. for removing air bubbles, prior to step (b). It is envisaged that the packaging container can be coated according to the methods described herein. Alternatively, the packaging container may already be coated, for example, with a material, for example, a hydrophobic material as described herein.

In more detail, the coating solution is preferably compounded, sterile filtered and dosed into the container (for example a glass vial) by using a micro piston pump. Devices, like Ti fixtures for example, are added and immersed into the protein solution. The containers are then furnished with stoppers which are only partially inserted prior to loading the containers into lyophilizer. To remove air bubbles possibly entrapped within pores of the titanium surface of the fixture, a vacuum of, for example, 30 hPa (which is above the boiling conditions of the protein solution at room temperature) is applied. Subsequently the chamber pressure of the freeze dryer is set to, for example, ≦500hPa, more preferably ≦250 hPa, most preferable ≦100 hPa and the solvent is removed by isothermal drying under nitrogen at ambient temperature (approx 25° C.). The vapour from the evaporated solvent is condensed at the ice condenser, set to very low temperature (for example approx. <−50° C.) as described in Murgatroyd K, The Freeze Dryer and Freeze Dryer Design, in Good Pharmaceutical Freeze-Drying Practice, 2, Cameron, P (ed.), Interpharm Press, Inc, Buffalo Grove Amsterdam, 1997. After drying, the chamber is evacuated to maximum vacuum and vented with sterile nitrogen before closing the devices within the freeze dryer by collapsing the lyo shelves together.

According to a second aspect, the present invention provides a packaging container for a device, wherein said packaging container is adapted such that said device is coatable directly within said packaging container. Thus, the container according to the present invention fulfils both functions, vessel for an in-situ coating process of the device (e.g. implant) and primary packaging system for long-term storage.

Preferably, the packaging container comprises a receptacle for receiving said device to be coated, said receptacle being adapted in size and shape to the size and shape of said device. It is preferred that the inner surface of said receptacle is coated, for example with a layer of an inert, repelling such as a hydrophilic or hydrophobic material, like silicone or PTFE or a PTFE like material in case of aqueous coating solutions. For the coating of hydrophobic surfaces with hydrophobic substances a hydrophilic coating on the vessel is necessary.

The coating of the inner surface ensures the quantitative deposition of the substance to be coated on the device or implant. This is highly advantageous in light of cost effective production of coated devices or implants.

According to a preferred design, the receptacle of the container is coaxially located within a container housing. The container housing comprises an opening for passing the device and the coating solution/substrate or substance through to the receptacle, and a bottom portion being located opposite to the opening. Furthermore, the receptacle comprises an opening for receiving the device and the coating substrate or substance, and a bottom portion being located opposite to its opening. The opening of said housing and the opening of said receptacle are aligned with each other, and the receptacle is attached at its bottom portion to the bottom portion of the housing. Preferably, the opening portion of the receptacle is spaced from the opening portion of the housing. It is preferred that the packaging container is made of glass. Alternatively, it is made of plastic material. Preferably, the outer dimensions of this glass container are identical to those of a standard type vial (DIN ISO 8362: Injektionsbehältnisse für Injektionspräparate und Zubehör). The inner dimensions are adapted to form a micro-vessel for coating and storage of devices such as Ti-fixtures, for example.

According to a third aspect of the present invention, a method of coating the inner surfaces of a packaging container for a device, preferably implants, to be coated by a substance, is provided comprising the steps of: (A) applying a hydrophobic material onto said inner surfaces of said container, and (B) heat-curing said applied material to form a baked-in layer on said inner surfaces of said container, wherein said coating influences the distribution coefficient of the substance to be coated on said device between said container and said device. As explained above, the hydrophobic material is preferably silicone or PTFE or a PTFE like material. In more detail, step (A) comprises siliconizing said inner surfaces of the container using silicone emulsion.

According to a fourth aspect, the present invention provides a coated device that is obtainable by a method according to the first aspect of the present invention. Preferably, the device is an implant, like a dental implant or a coronary stent. For example, the implant is a stent, a nail, a screw, a cage, or a plate, respectively.

Thus, the coated device of the fourth aspect is characterized by the features, which are contributed by the aforementioned method of the first aspect of the present invention. In particular, the device comprises an osteoinductive protein which is homogenously coated on a metal or alloy porous or non-porous surface of the device, whereby the oxidation status of the osteoinductive protein is not significantly increased in comparison to osteoinductive protein which has not been coated onto the said metal or alloy surface.

The present invention further encompasses the use of the method of coating a device according to the first aspect of the present invention for improving the homogeneous distribution of the coating on the device.

The present invention also encompasses the use of the method of coating a packaging container according to the third aspect of the present invention for improving and/or controlling the distribution coefficient of the substance to be coated on said device between said container and said device.

The present invention also encompasses a kit comprising the device which is obtainable by the method of the first aspect of the present invention. The definitions and explanations of the terms made before in context with the methods, devices, and uses of the present invention apply mutatis mutandis for the kit described herein. The parts of the kit of the invention can be packaged individually in vials or other appropriate means depending on the respective ingredient or in combination in suitable containers or multi-container units. Manufacture of the kit follows preferably standard procedures which are known to the person skilled in the art. Preferably, the device is packaged in a container or vial in a oxygen free atmosphere, such as an inert gas atmosphere, preferably consisting of nitrogen.

The present invention is described in the following with reference to the accompanying drawings, in which:

FIG. 1 schematically shows the coating method according to the first aspect of the present invention for titanium;

Figure 5:
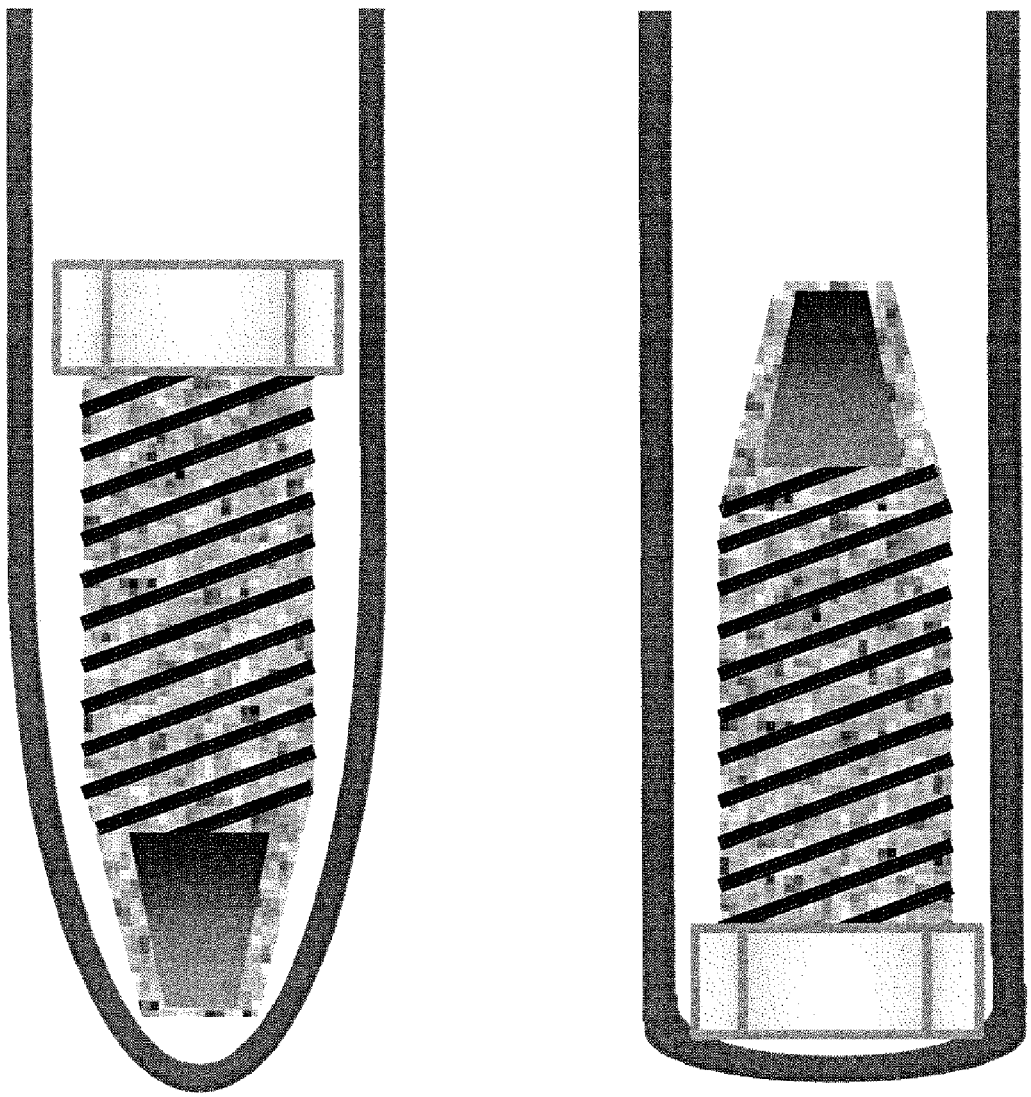
Figure 6:
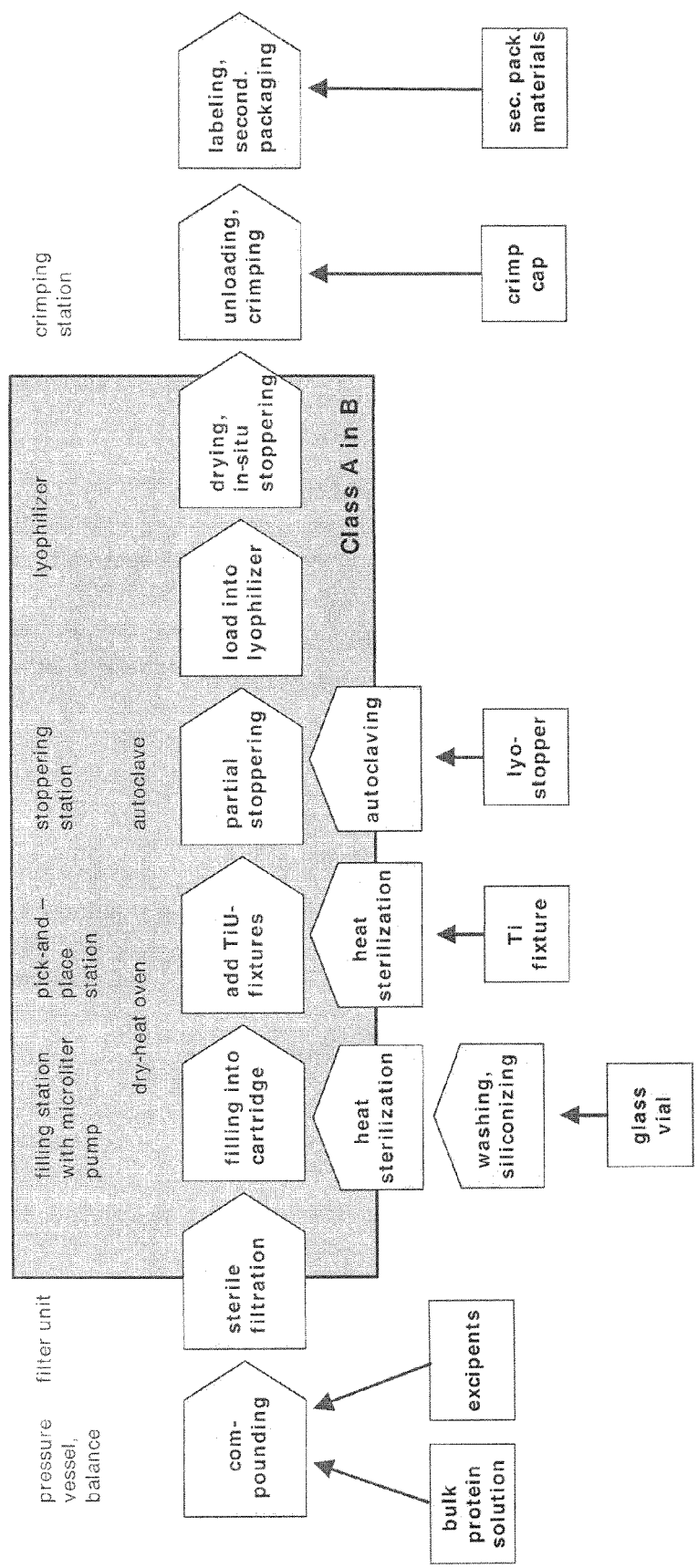
Figure 7:
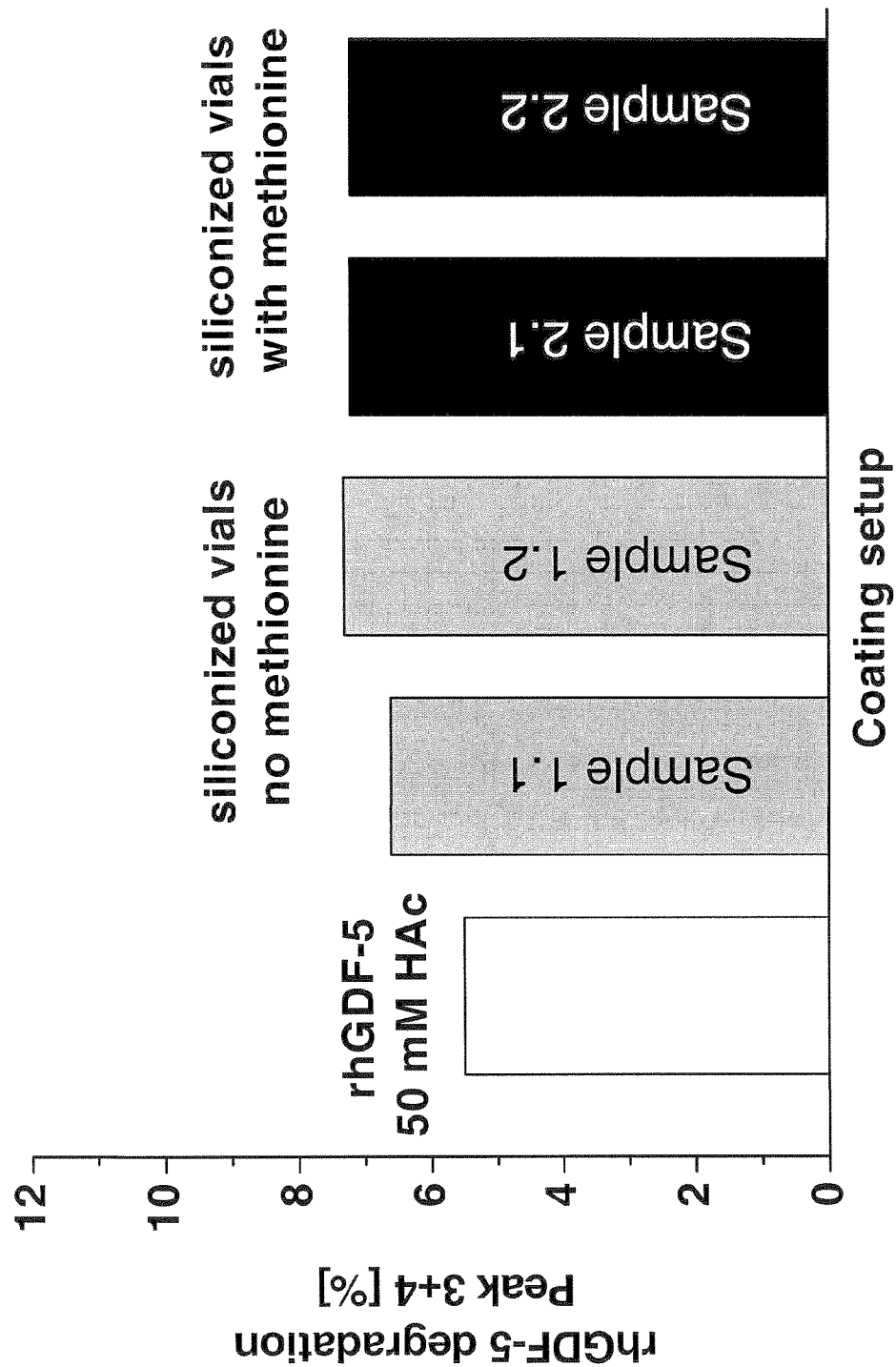
Figure 8:
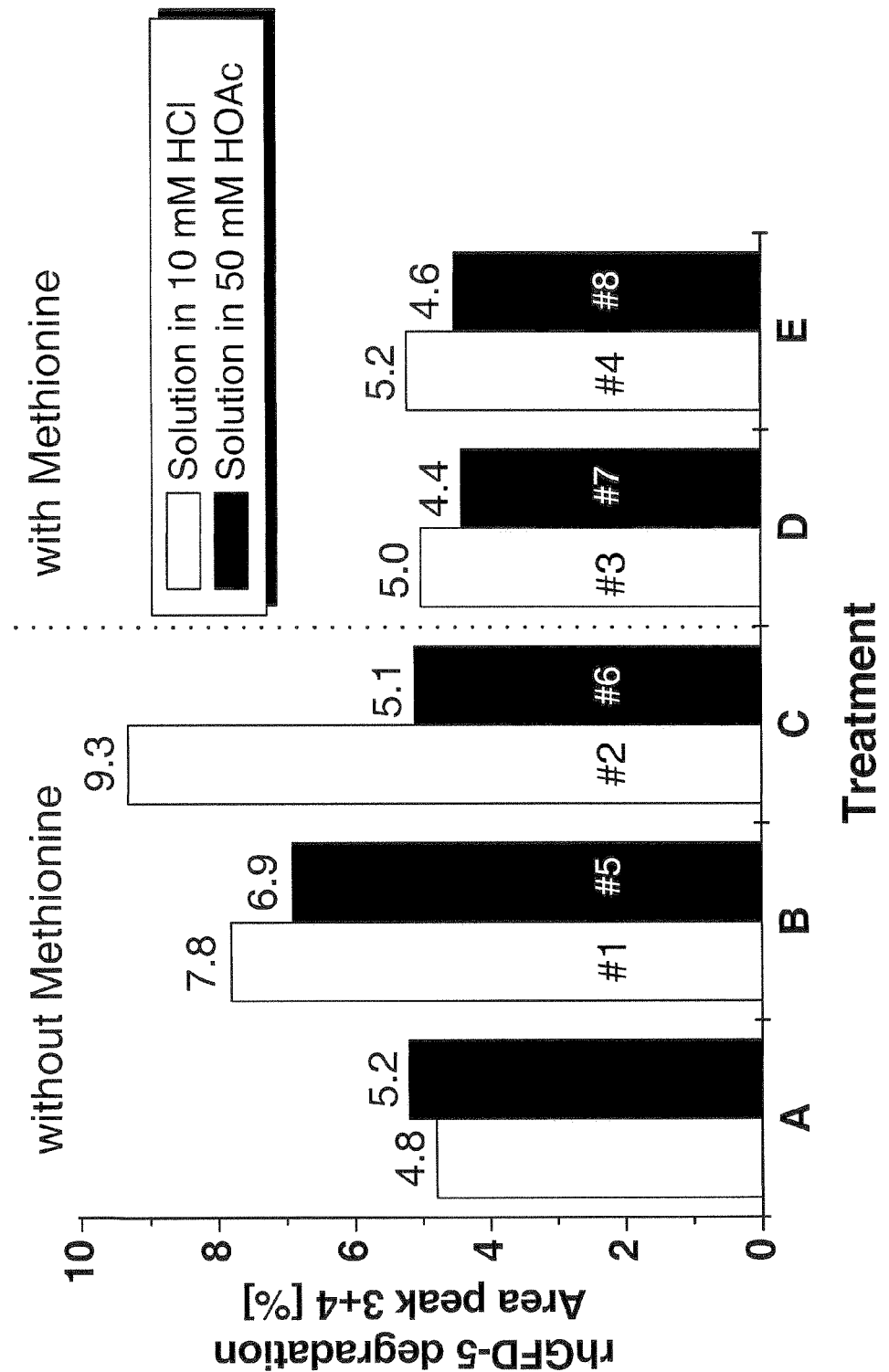
Figure 9:
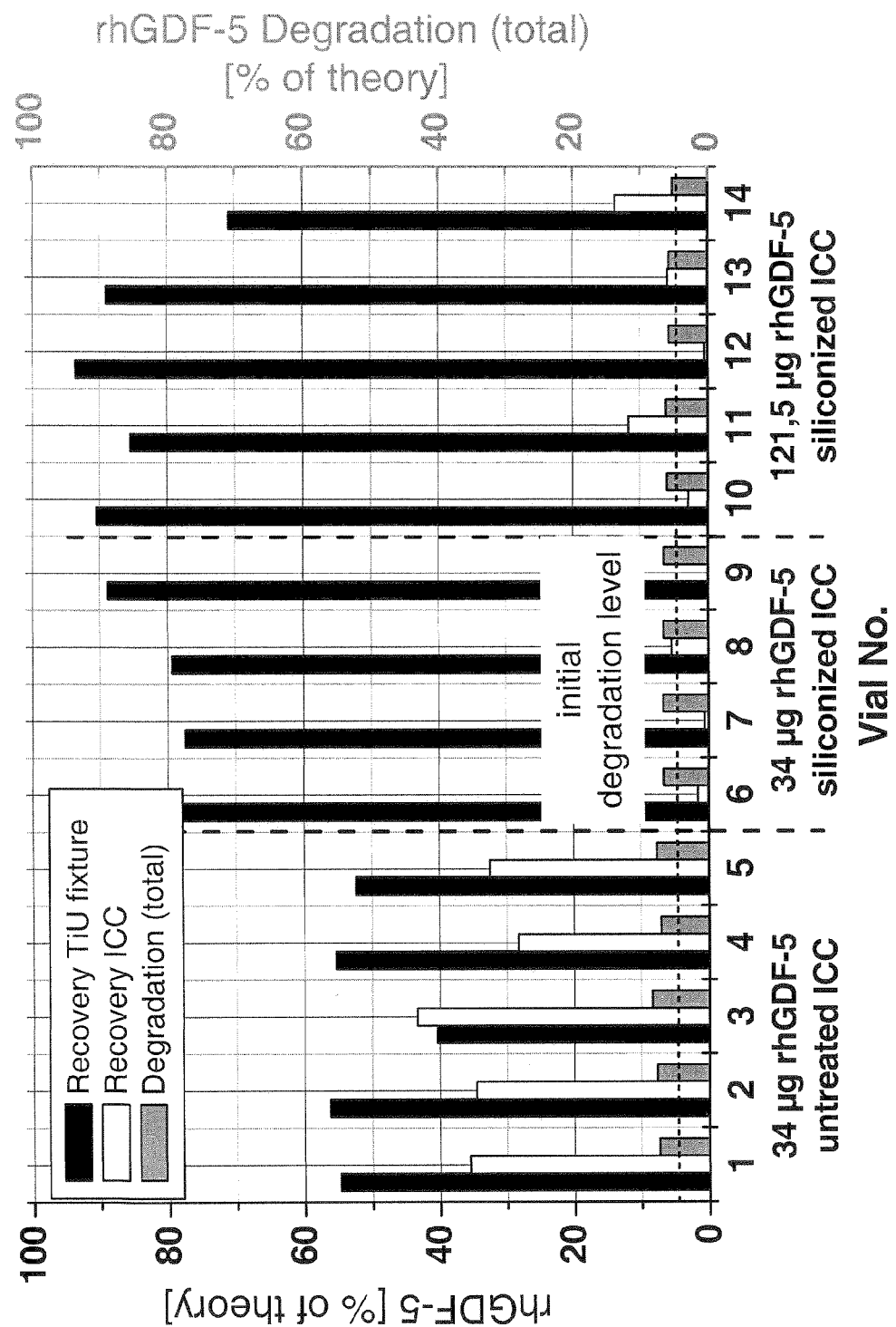
Figure 10:
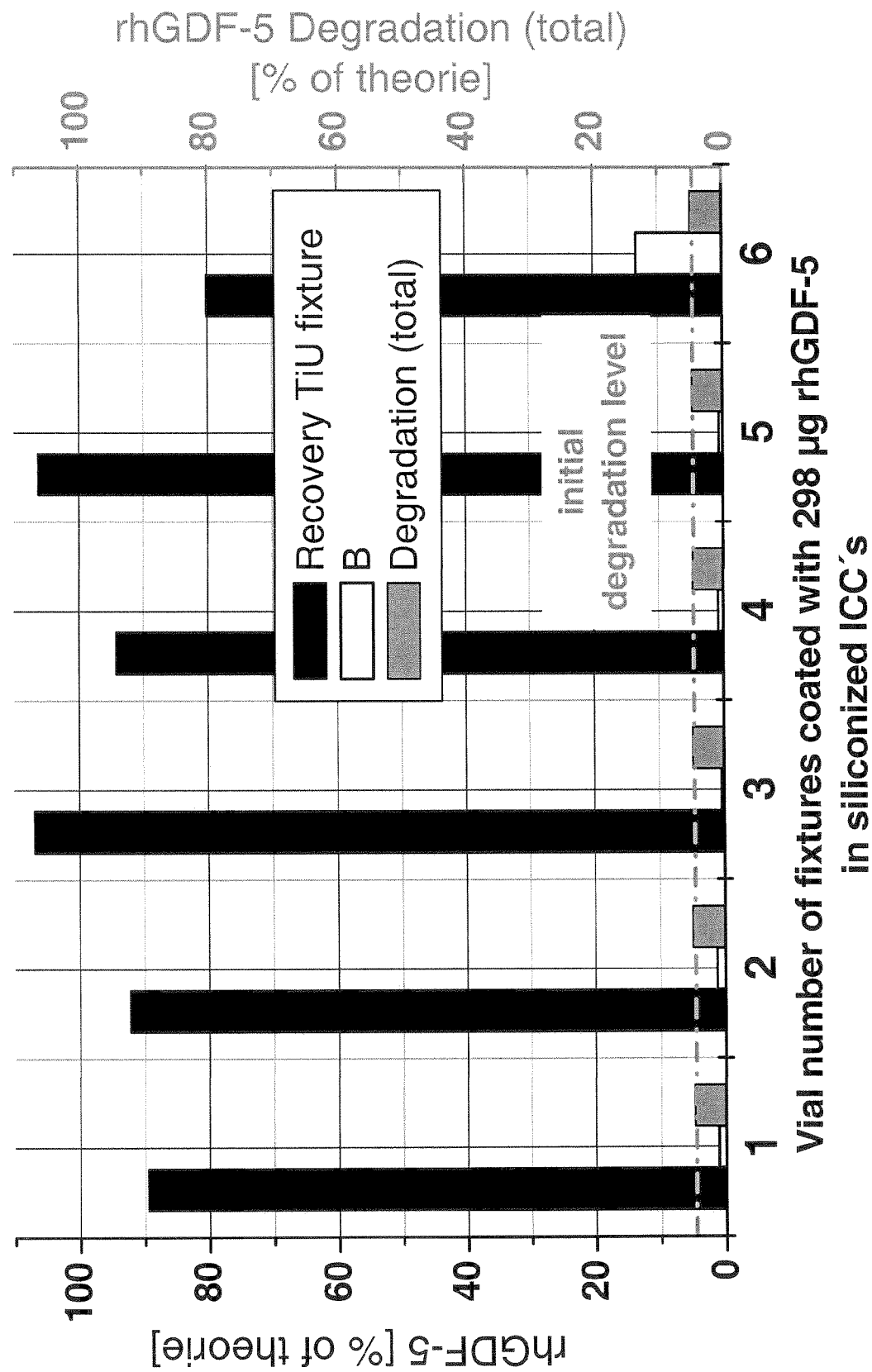
Figure 11:
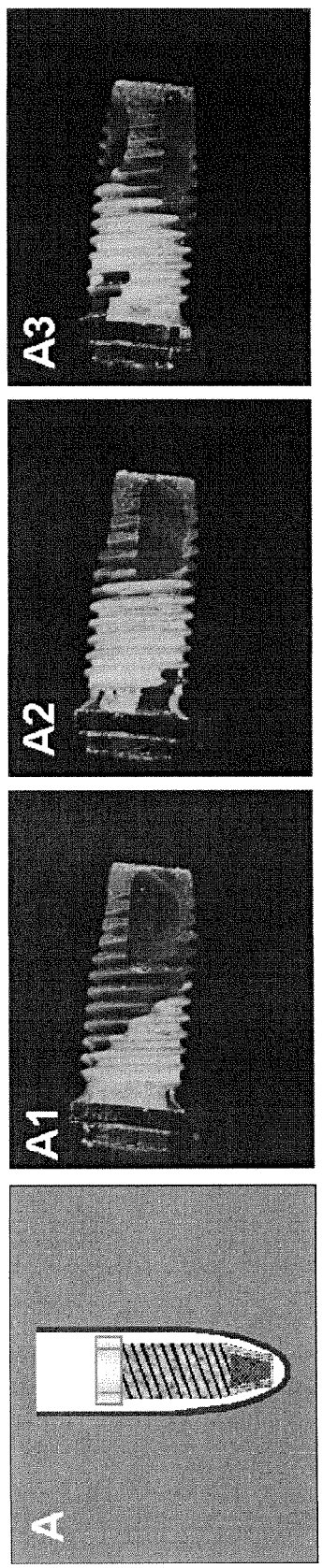
Figure 12:
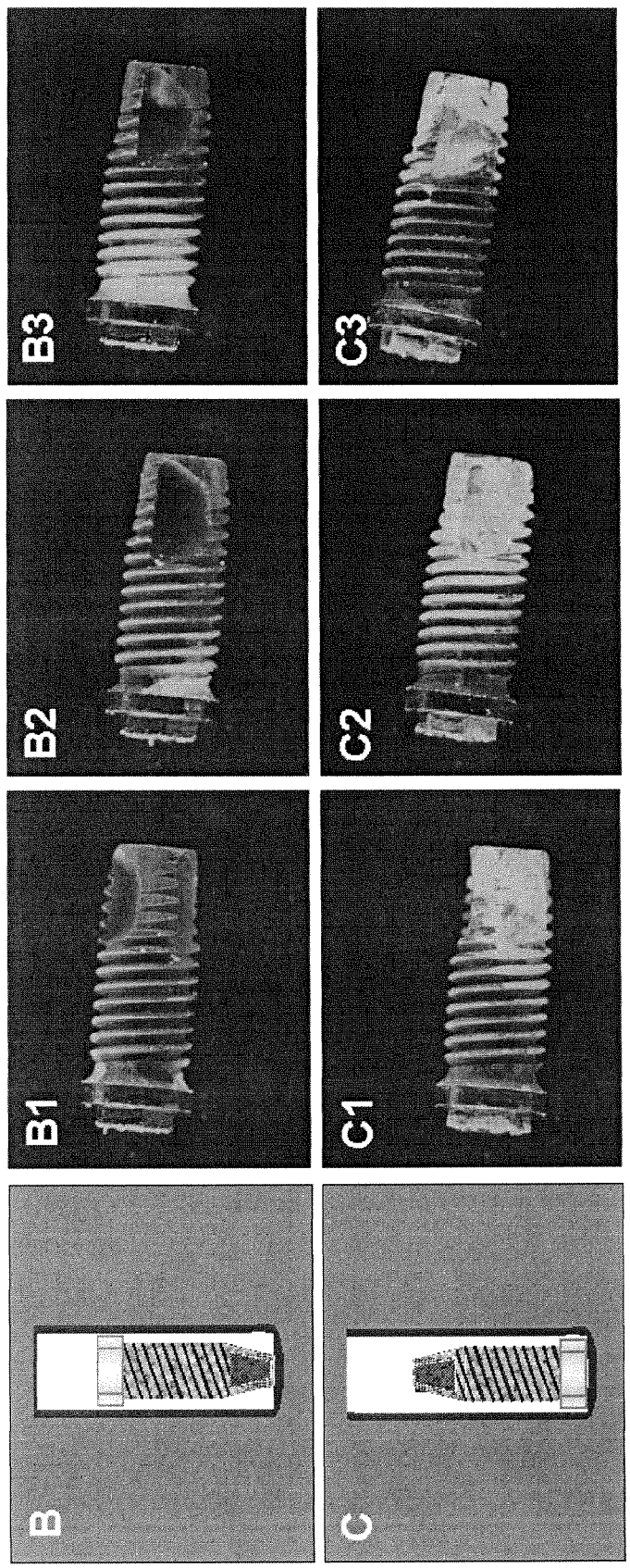
Figure 13:
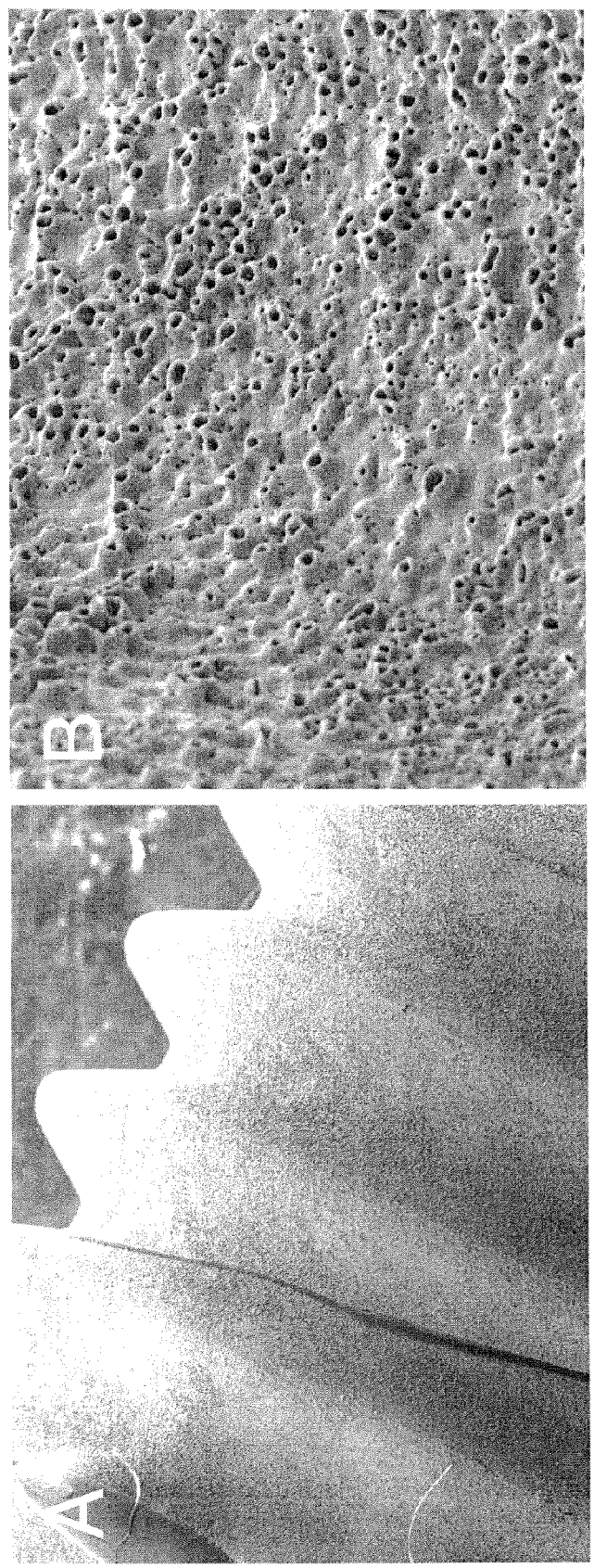

FIG. 5 schematically shows containers containing a device to be coated: upright (left) and upside down (right);

FIG. 6 shows the coating method adapted in an aseptic process according to the first aspect of the present invention by means of a manufacturing flow chart;

FIG. 7 shows the protective effect of methionine onto protein stability;

FIG. 8 shows the protective effect of methionine onto rhGDF-5 stability by RP-HPLC-analysis of different rhGDF-5 formulations (with and without methionine); TiU=TiUite;

FIG. 9 shows the effect of unsiliconized vs. silliconized container onto protein distribution (content of protein on the implant black bar vs. loss in the container white bar) and reduced degradation of the protein by (RP-HPLC-analysis) first aspect of the; TiU=TiUite; ICC=immerse-coating cartridge;

FIG. 10 shows the distribution and degradation of rhGDF-5 coated onto titanium implants with maximum rhGDF-5 loading (RP-HPLC-analysis); ICC=immerse-coating cartridge;

FIG. 11 shows the distribution of rhGDF-5 dried at atmospheric pressure under non-optimized conditions by using fluorescence staining;

FIG. 12 shows the homogenous distribution of rhGDF-5 adsorbed onto the implant surface by fluorescence staining of fixtures dried after optimizing the drying conditions; and FIG. 13 shows SEM pictures of the porous implant surface (Fig A 100×, Fig B 1000×).

DETAILED DESCRIPTION OF THE PRESENT INVENTION

Figure 1:
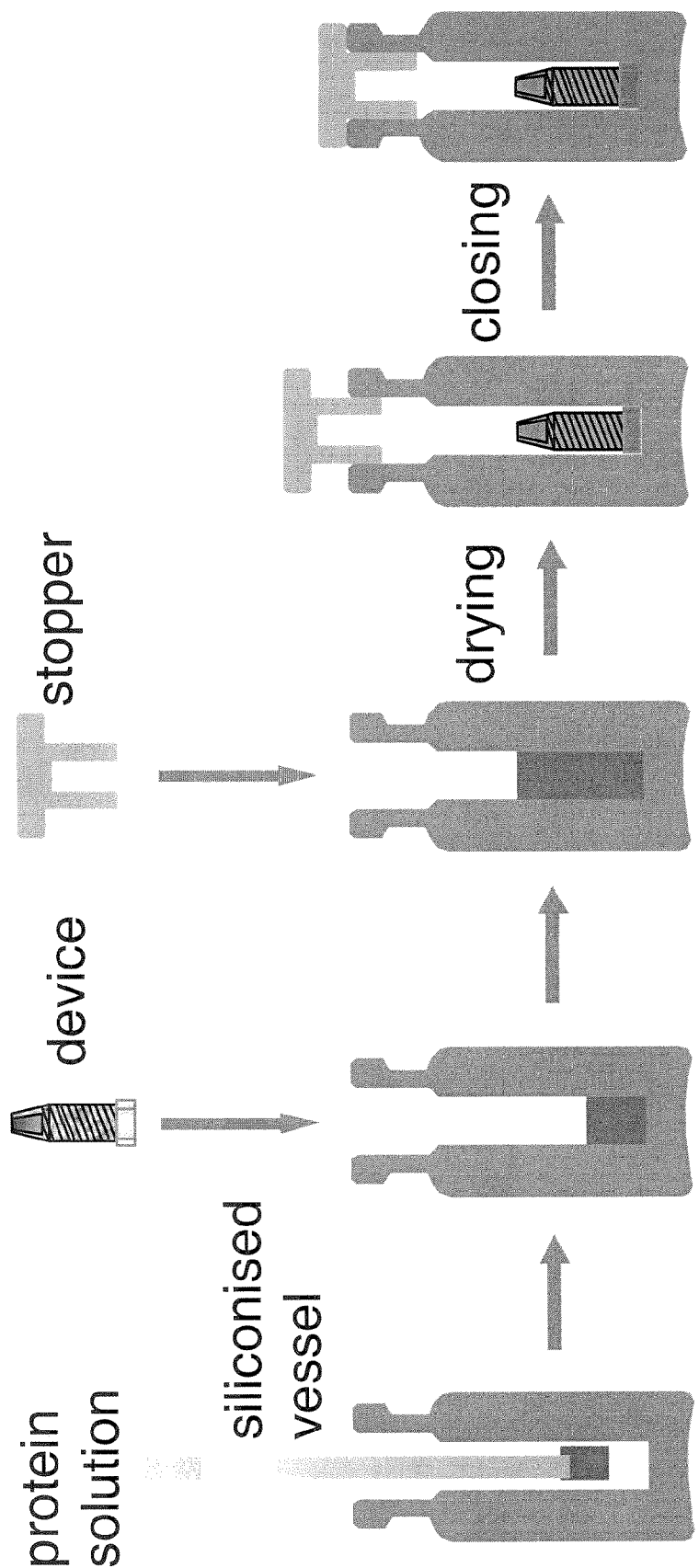

FIG. 1 schematically shows the coating method according to the first aspect of the present invention used for coating of titanium fixtures. The packaging container used according to the present invention for coating of the implant (here: titanium fixture) is shown in FIG. 1 in five process steps. In the first step, protein solution is added to the container, which in the preferred embodiment of FIG. 1 is a siliconized vessel. Thereafter, the device, e.g. an implant like a screw is inserted into the container and thus completely surrounded by the liquid. In the third step, a stopper is used to close the container. However, the stopper is not placed in its final closing position (which is shown in the most right drawing of FIG. 1) but in an intermediate position. Having the stopper partially inserted into the container, the drying process is started which results in the device being coated. Due to the semi-closed position of the stopper, it is possible that for example water can escape from the container during the drying process. After the drying/coating procedure the chamber of the lyophilizer may be vented with sterile nitrogen or with any other inert gas before completely closing the containers by depressing the stopper into the container. Alternatively a vacuum can be applied prior to closing the containers. The fully coated implant is already contained in the packaging container and ready for shipment.

Figure 2:
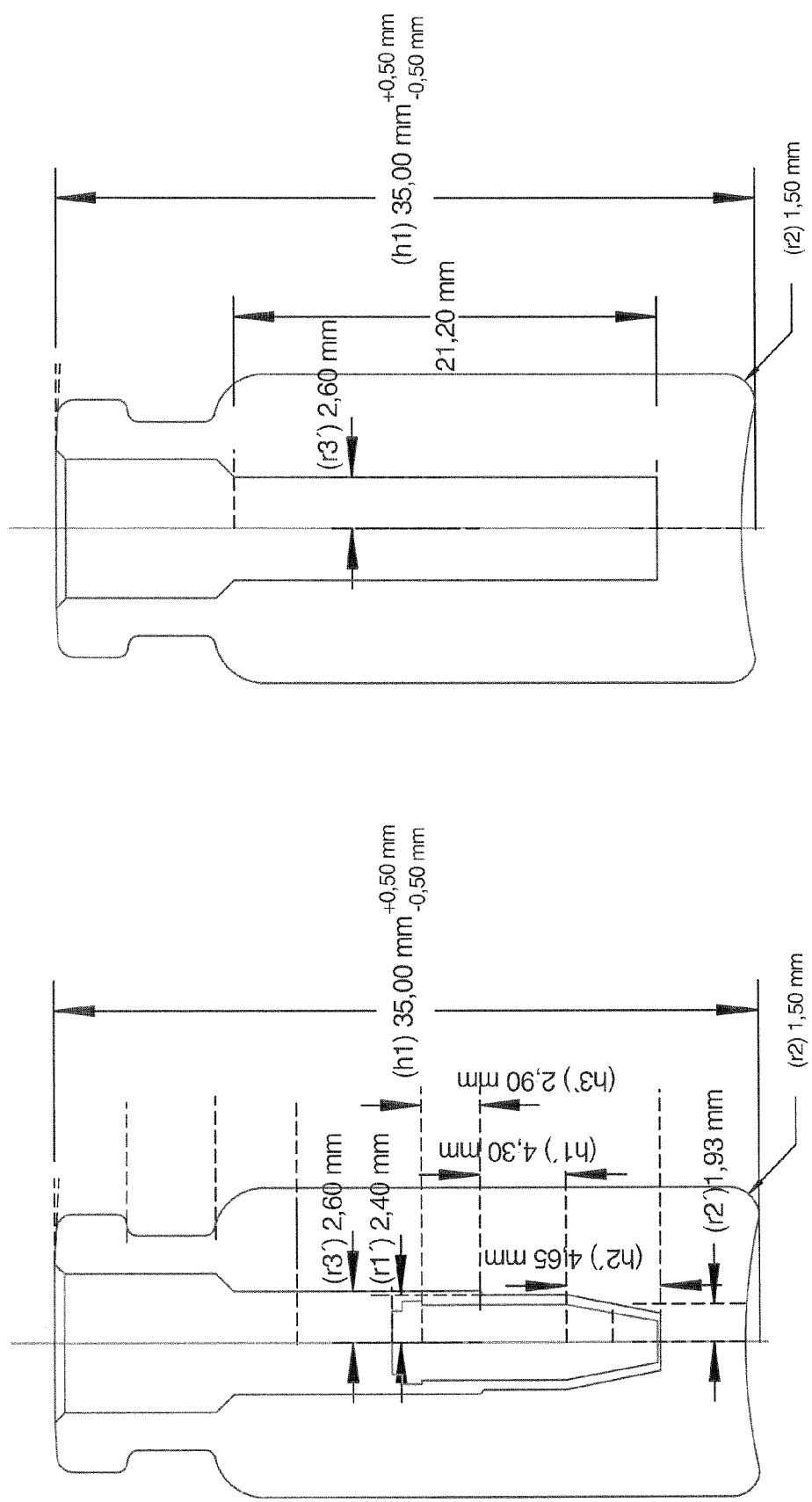
FIG. 2 shows a cross-sectional view of a preferred container according to the second aspect of the present invention.

FIG. 2 shows a further alternative container according to the second aspect of the present invention. This packaging container comprises a specially designed solid glas vial. The outer dimensions of this glass vial are identical to those of a standard 2R vial. The inner dimensions are adapted to form a micro-vessel for coating and storage of, for example, Ti-fixtures. This glass vial is siliconized using medical grade silicone emulsion baked into the glass by heat treatment.

Figure 3A:
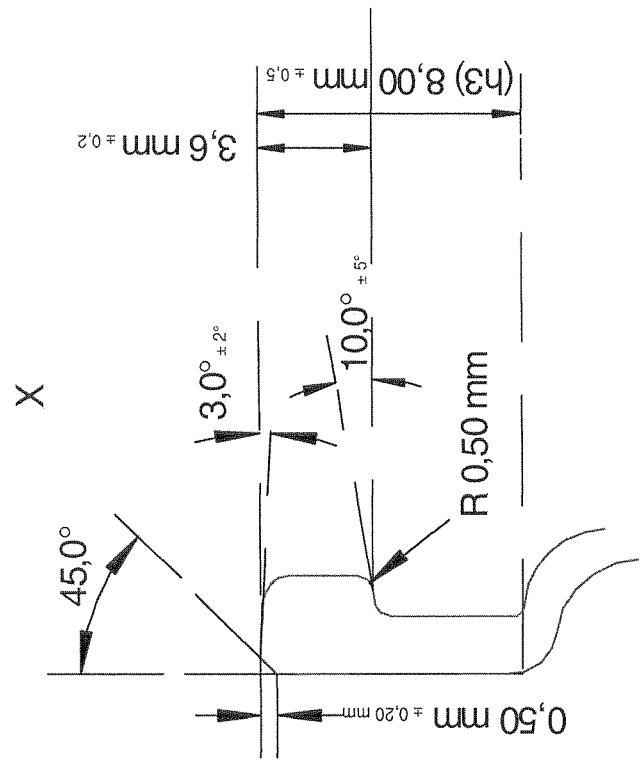
FIG. 3 shows a further alternative container according to the second aspect of the present invention.
Figure 3A:
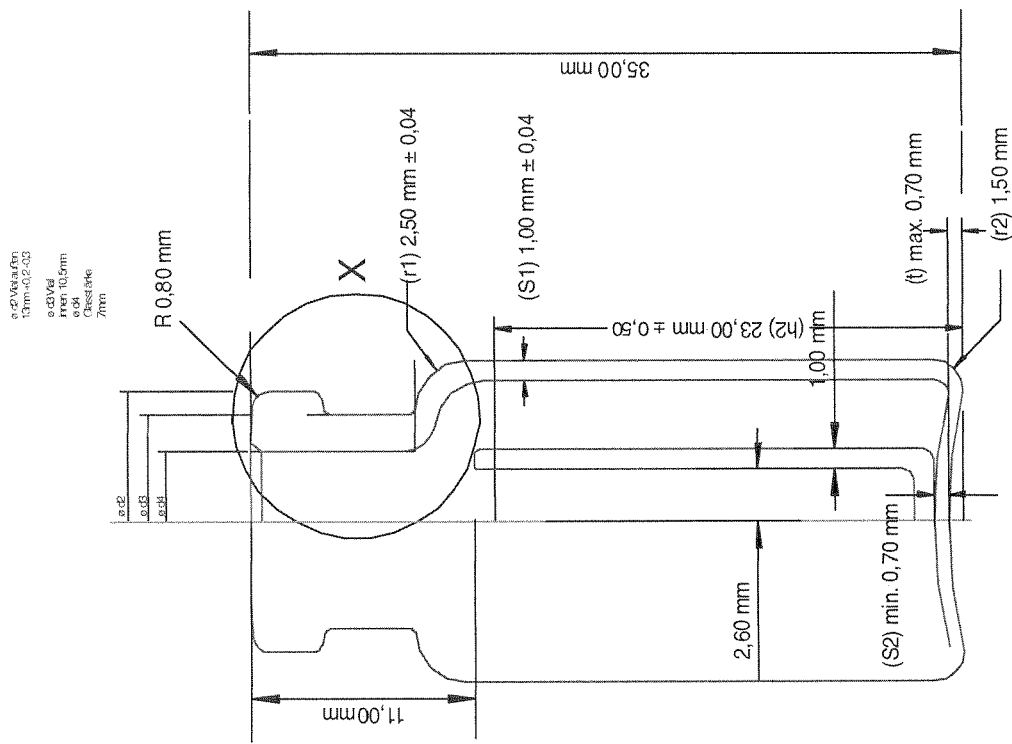
Figure 3B:
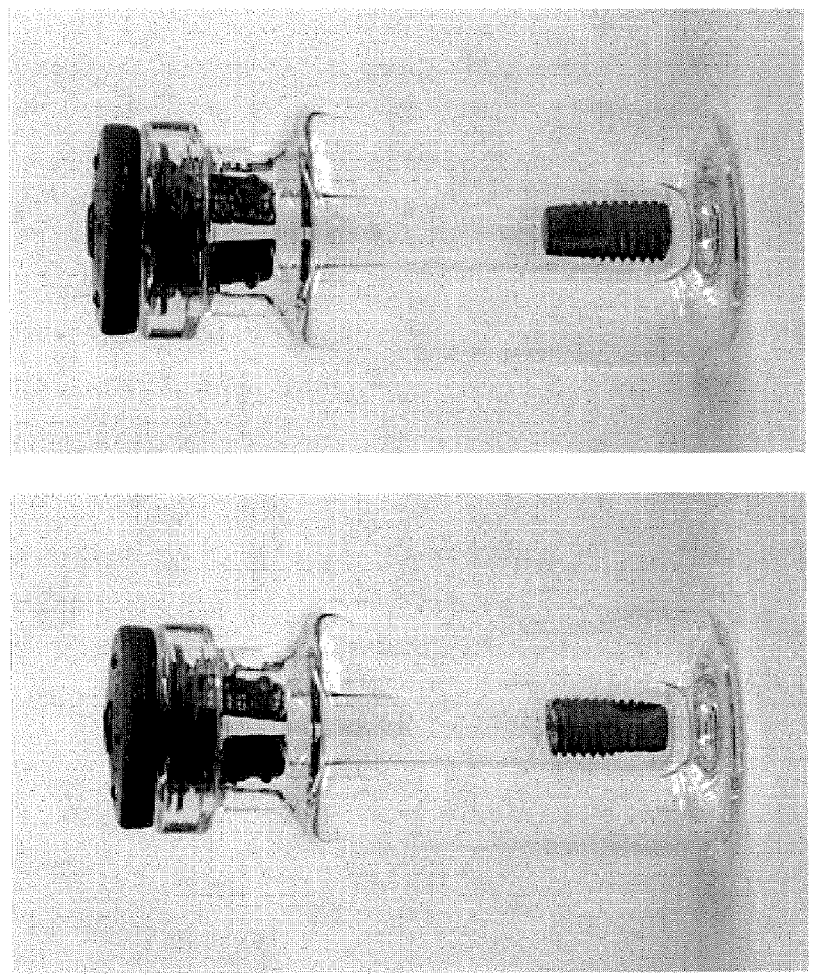

FIG. 3 shows a cross-sectional view of a preferred container according to the second aspect of the present invention. This preferred packaging container consists of a standard 2R type glass vial with an inner glass tube firmly molded onto the bottom of the vial (one-component glass vial). By means of this glass tube a micro vessel is created for coating of implants (like Ti-fixtures) in upside-down position. The vial is siliconized according to the present invention using medical grade silicone emulsion being baked into the glass by heat treatment.

Figure 4:
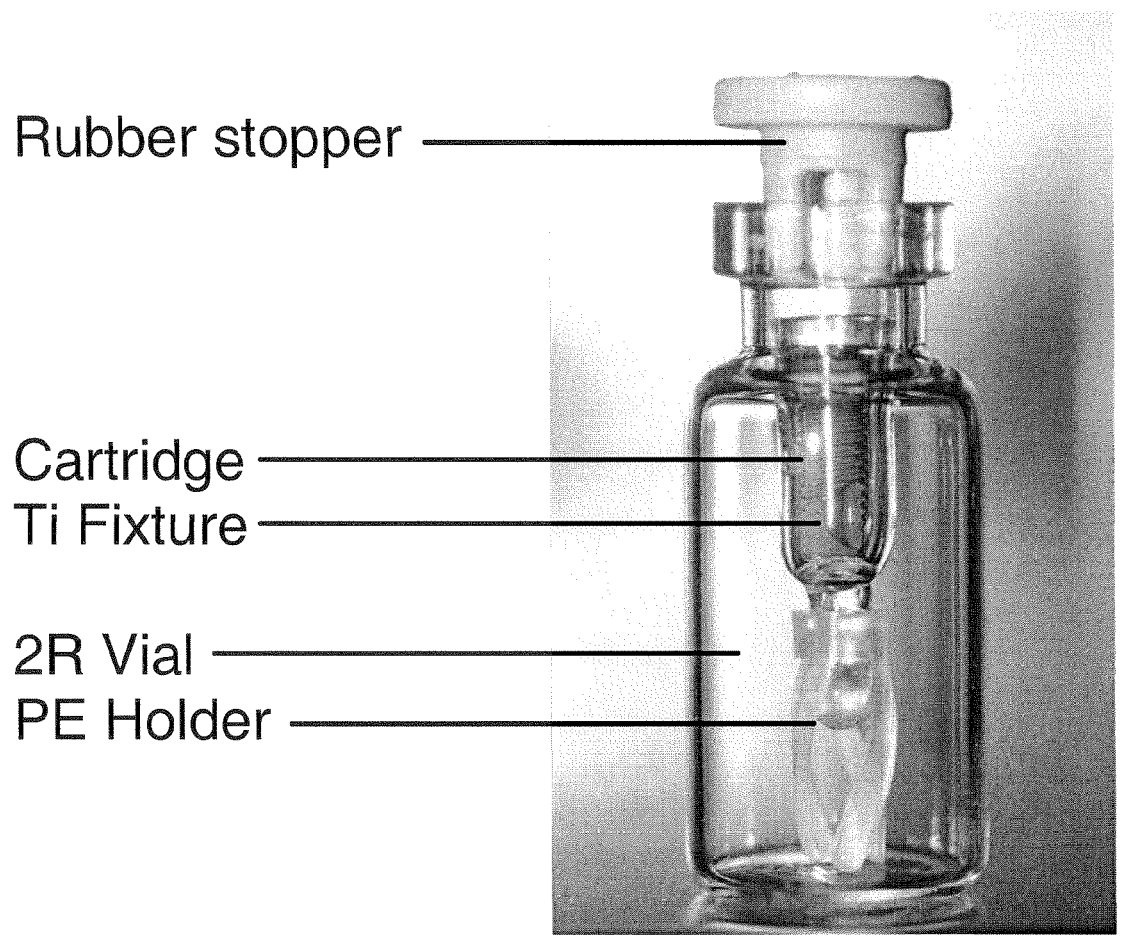
FIG. 4 shows a further alternative container according to the second aspect of the present invention.

FIG. 4 shows a further alternative container according to the second aspect of the present invention. This container comprises a standard 2R glass vial, a standard bromobutyl lyo-stopper, a heat siliconized micro glass-cartridge within the vial, and a flexible plastic holder (PE) for the cartridge. The vial is preferably sealed by crimping with an aluminum cap (not shown).

Cartridges are siliconized using medical grade silicone emulsion, baked into the glass by heat treatment (see also chapter 4.3 Process).Vials are washed and siliconized using silicone emulsion. Heat curing to form a baked-in silicone layer and to sterilize the vial is done at a temperature of 250° C. minimum. Plastic holders are manually attached to the cartridges, placed into the vial.

FIG. 5 schematically shows alternative container designs of containers containing a device to be coated upright (left drawing) and upside down (right drawing). In both alternatives, the shape of the container is adapted to the shape of the implant, which ensures effective coating. Experiments have shown that coating in upside down position leads to a more homogenous protein layer on the surface of the fixtures. This is due to the complex geometry of the device and the fact that air bubbles, which arise during lowering the pressure can lead to coating defects. Those air bubbles are easily entrapped at the bolt head of the fixture when it stands in an upright position but can escape the cartridge when the fixture is placed upside down.

FIG. 6 shows the coating method adapted in an aseptic process according to the first aspect of the present invention by means of a manufacturing flow chart. In the first step, i.e., the compounding step, the bulk protein solution and the excipients are brought together. Thereafter, a sterile filtration takes place. This is done by using a filter unit. The glass vial, i.e., the container is first washed and siliconized, thereafter heat sterilized, and finally placed in the filling station. In the filling station, the solution is filled into the container, for example using a micropiston pump. In a subsequent pick-and-place station, the i.e. heat-sterilized fixtures are placed in the container which contains the solution of the coating material. Subsequently the containers proceed to the stoppering station and are partially closed by autoclaved lyo-stoppers. This assembly is then loaded into a lyophilizer where the drying and subsequent final stoppering is performed. At a crimping station, the containers are sealed with a crimp cap. The last step comprises labelling and secondary packaging for shipment. Rubber components, i.e. lyo-stoppers are standard type lyo-stoppers. The vials are preferably sealed with Flip-Tear up standard type crimp caps.

FIG. 7 shows the protein degradation quantified by RP-HPLC of titanium implants coated with rhGDF-5 (used coating solution rhGDF-5 in 50 mM acetic acid, and rhGDF-5 in 50 mM acetic acid with 10 mM methionine). Only a minor increase of protein degradation can be observed compared to the starting material. This shows the feasibility of the coating method of the present invention.

FIG. 8 shows the stability of two protein solutions (rhGDF-5) in different coating solutions, 10 mM HCl (white bar) vs. 50 mM acetic acid (black bar), both with and without methionine while being in contact with the implant to be coated for up to 7 hours. The data show that it is possible to avoid protein degradation when the formulation is adapted to the coating process (50 mM acetic acid with 10 mM methionine). Additionally this experiment is a first prove of concept for the intended large-scale manufacturing process were a stability of the coating solution is a prerequisite to ensure a consistent product quality. A=GDF-5 starting solution; B=GDF-5 solution after 7 h, C=GDF-5 solution+TiU fixture, D=GDF-5 solution+Meth. After 7 h, E=GDF-5 solution+Meth.+TiU after 7 h.

FIG. 9 shows the effect of using siliconized container for the coating. The obtained data shown in FIG. 9 clearly indicate the advantages, regarding the protein distribution between the container and the implant.

While for untreated container more than 30% rhGDF-5 remains in the container, this amount can be massively reduced down to 5% if siliconized containers were used. This effect is mostly independent from the absolute rhGDF-5 load and is reproducible as is shown for two different protein amounts (34 µg, 121.5 µg per fixture)

FIG. 10 shows the distribution of rhGDF-5 dried at atmospheric pressure. To avoid the formation of bubbles, a first experiment was performed, drying the implant without applying of vacuum. Thus, drying was achieved by condensation of water onto the ultra-cold ice-condenser only. FIG. 10 also shows that even with an increased coating dosage up to 298 µg rhGDF-5 per implant the protein distribution between the container and the implant is still nearly quantitatively on the implant. These finding demonstrate that the protein distribution is independently from the coating dosage which is a further advantage of the coating method of the present invention.

FIG. 11 shows the corresponding fluorescence analysis of the so dried fixtures. It can be noted from the pictures that the protein is much more segregated between the head of the fixture were the rhGDF-5 is obviously concentrated and the lower part. Interestingly, the coating seems to be relatively homogeneous over the corresponding radius.

FIG. 12 shows the homogenous distribution of rhGDF-5 adsorbed onto the implant surface by fluorescence staining of fixtures dried after optimizing the drying conditions. In an attempt to optimize the coating conditions, some parameters that have an effect on the protein distribution were varied:
- the pressure; to allow a complete wetting also inside cavities of the micro structured fixture surface. It was changed from a constant pressure to a pulsed vacuum;
- the position of the fixture in the container upside vs. upside down because the conic shape of the fixture allows air bubbles to escape the container more easily; and
- the shape of the container.

The pictures demonstrate that fixtures, dried in up-side down position have an advantageous radial symmetric coating with some protein concentration at the taper of the fixture.

FIG. 13 shows SEM pictures of the porous titanium implant surface (Fig A 100×, Fig B 1000×) which were used for the described coating with rhGDF-5.

EXAMPLE 1

Quantification of GDF-5 in Solution by RP-HPLC

The GDF-5 content was determined by reversed phase (RP-) HPLC-analysis. Aliquots of the sample were analyzed using a Poros C8-18 column (R2/10, 2.1*30 mm, Applied Biosystems), 0.1% formic acid in 21% acetonitrile (solvent A) and 0.1% formic acid in 84% acetonitrile (solvent B) were used as solvents at a flow rate of 0.4 ml/min. The elution profile was recorded by measuring the absorbance at 220 nm. The amounts of GDF-5 were calculated form the peak area at 220 nm using a standard curve.

EXAMPLE 2

Extraction and Quantification of the Immobilized Protein

The protein was extracted by incubation of the coated device first in 10 mmol/l HCl for 3 h at room temperature. After adjusting the PBS sample to pH 2. The HCl solutions containing extracted bone growth factor were analyzed by RP-HPLC as described in example 1.

EXAMPLE 3

Determination of Chemical Modifications of the Extracted Protein

The amount of chemical modifications i.e. oxidation of bone growth factor in solutions containing extracted protein was determined by RP-HPLC. The sample is applied to a Vydak C8-18 column (2×250 mm) which has been equilibrated with 0.15% TFA, 20% acetonitrile. After washing of the column, the elution of the bone growth factor takes place with a mixture of 0.1% TFA, and a stepwise gradient of 20%-84% acetonitrile (flow: 0.3 ml/min). The elution is observed by measuring the absorption at 220 nm. The quantification takes place via the ratio peak area of modified species in relation to the total peak area.

EXAMPLE 4

Determination of the Homogeneity Coating of Bone Growth Factor on Titan Surfaces by Fluorescence Microscopy We investigated the coating homogeneity of rhGDF-5 on the titanium implant by using a fluorescence marker for proteins. The determination was performed by fluorescence microscopy.

Fluorescence dying of the immobilized protein:
The coated devices were prepared as described in example 5. For dying 2.3 µl of a 10 mmol/l solution of Alexa Fluor™ 488 were added to 1 ml of a 0.15 M NaHCO3 solution. The implants were incubated in 1 ml of the fluorescence dye mixture in the dark for 4 h at room temperature. The ratio protein:fluorophor is 1:10. The implant used as blank was incubated for 20 min only. After the incubation period the implants were extensively washed with demineralized water and dried for 15 min under vacuum in the dark.

The fluorescence signal was detected by fluorescence microscopy and documented by an imaging software.

In FIGS. 11 and 12 the distribution of rhGDF-5 can be clearly determined by fluorescence microscopy. Meaning the fluorescence marker bound to the protein. To exclude any effects of the solvent we also prepared an implant that was not coated with rhGDF-5 but also incubated in Fluorescence marker Alexa Fluor™ 488 (Data not shown).

EXAMPLE 5

Coating of Titanium Implants with rhGDF-5

The objective of this example was to demonstrate the feasibility of this coating method. In more detail it was tested, whether methionine as an anti-oxidation preservative excipient has a beneficial effect on the rhGDF-5 degradation rate.

The test coating was performed by two different experimental setups and with two fixtures per setup. The first tested setup was carried out with the freshly reformulated rhGDF-5 in 50 mM acetic acid. In the second setup a rhGDF-5 coating solution in 50 mM acetic acid was tested, which additionally contains methionine to evaluate the possibility of minimizing the oxidation rate. Table 1 gives an overview of the tested coating setups. All samples were dried in the freeze-drier for four hours at approx. 66 mbar with the ice condenser set to approx. −80° C. The freeze-drying shelves were kept constantly at ambient temperature of approx. 20° C., thus freezing and freeze-drying did not take place. Effective drying was achieved by evaporation of the solvent and condensing of the solvent vapour at the ultra cold ice-condenser.

TABLE 1

Scheme of the tested Samples

| Sample-No. | Description |
|---|---|
| 1.1 | Siliconized vial |
| 1.2 | Siliconized vial |
| 2.1 | Siliconized vial + Methionine |
| 2.2 | Siliconized vial + Methionine |

Results

The findings concerning the rhGDF-5 degradation of the two experiments are summarized in FIG. 7. The increase of degradation was measured according to the method described in example 2.

The comparison between coating solutions with or without addition of methionine surprisingly shows no significant difference concerning the rhGDF-5 the formation of degradation products. In both cases only a slight increase of protein degradation is observed (<2%). This can be explained by a stabilizing effect of the acetic acid, which may act as a radical scavenger and therefore affect as a short-term protective agent. However, this non-influence of methionine is only the case under ideal conditions under small scale manufacturing. Under example 7 where large scale manufacturing has been established and longer holding times for example 7 hours within the manufacturing process are unavoidable, these increased degradation of the protein can be avoided by using methionine.

In summary, these results demonstrate the successful coating of rhGDF-5 onto the surface of an metallic implant. Furthermore, the proof of concept of an isothermic drying method has been demonstrated.

EXAMPLE 6

Method for Coating Titan or Titan Alloy with Bone Growth Factor Manually in Laboratory-Scale The coating process is performed under an inert gas atmosphere to exclude oxygen. To maintain these conditions a chamber is used. The chamber consists of a hermetically closed room with a continuous stream of inert gas, e.g. $N_2$ gas. Inside the chamber a slight excess pressure is maintained. The materials needed for the coating process are transported into the chamber through an air-lock. The chamber allows a manually coating process. For the definition and standardization of the coating process the relative humidity in the chamber is monitored and adjusted.

Coating:

Titan sheets were cleaned, washed with demineralized water and dried. The titan sheets were coated with 60 µg of rhGDF-5. Each sheet was laid down flat in a dish and coated with rhGDF-5 solution onto one side of the metal sheet. Coating was performed under $N_2$ gas atmosphere in a chamber as described above and at a temperature of 0° C. to 4° C. After coating the sheet was dried at the respective conditions for 30 min under vacuum.

Extraction:

rhGDF-5 was incubated first in PBS to mimic near physiological conditions. To keep samples nearly free of oxygen, the PBS solution was saturated with $N_2$ gas for the respective samples.

After PBS incubation the sheets were incubated in 10 mmol/l HCl for 3 h at the respective temperature. The rhGDF-5 in the extraction solutions was quantified by RP-HPLC (see example 1). The amount of oxidized rh-GDF-5 was also determined by RP-HPLC (see example 2).

To be able to compare samples coated and extracted as described above, the same procedure was performed at room temperature and under oxygen atmosphere.

TABLE 2

| Sample | Atmosphere | Temperature | % oxidized protein after extraction (Mean) | SD |
|---|---|---|---|---|
| Implant | air | RT | 10.0 | 1.6 |
| Implant | N2 | 4° C. | 5.6 | 0.6 |
| Bulk | air | RT | 4.7 | 0.0 |

The parameters tested in the experiments here have an influence on the amount of oxidized rhGDF-5 after extraction from the titan sheets: Samples coated in the presence of air oxygen at room temperature reveal an amount of oxidized rhGDF-5 of 10.0%±1.6% as displayed in table 2.

The samples processed at 4° C. and under N2 gas show 5.6%±0.6% oxidized rhGDF-5 after extraction. Compared to rhGDF-5 bulk solution the samples processed at 4° C. and N2 gas reveal no significant difference in the amount of oxidized rhGDF-5 (4.7%±0%).

EXAMPLE 7

Evaluation Industrial Scale Process

The following experiments demonstrate the suitability of the developed coating method for the industrial-scale manufacturing of coated implants using the siliconized containments.

In a first step the rhGDF-5 bulk solution was reformulated into two different acidic formulations with and without addition of methionine. The formulations were tested in terms of their feasibility and stability in the siliconized containment during manufacturing. To identify and quantify the degradation caused by the titanium fixture, all formulations were tested with and without addition of a fixture to the solution filled into the siliconized containment. An overview of the experimental set-up is given in table 3 below.

To simulate industrial-scale manufacturing, the solutions were incubated for seven hours at 23° C. under normal air atmosphere (worst-case scenario). The resulted extend of protein degradation was quantified afterwards by RP-HPLC analysis.

TABLE 3

Scheme of the different tested rhGDF-5 formulations

| | rhGDF-5 in 10-mM HCl | | rhGDF-5 in 50 mM acetic acid | |
|---|---|---|---|---|
| | Without 10 mM Methionine | With 10 mM Methionine | Without 10 mM Methionine | With 10 mM Methionine |
| Solution in siliconized containment | #1 | #3 | #5 | #7 |
| Solution in siliconized containment + implant | #2 | #4 | #6 | #8 |

Results

The obtained RP-HPLC data are shown in FIG. 8. The data for the rhGDF-5 formulation in 10 mM HCl (red columns) show that a storage over 7 hours already affects an increase of the amount of rhGDF-5 degradation products from an initial percentage of 4.8% up to 7.8%. In the presence of a titanium fixture the value further increased up to 9.3%.

A completely different result is obtained for the solutions containing methionine. The analysis shows a clear beneficial effect of this excipient on the degradation rate of rhGDF-5. Neither the solution alone nor the solution with titanium fixture show a significant increase of oxidation/deamidation.

The also investigated rhGDF-5 formulation in 50 mM acetic acid gives quite similar results. Although the initial value is with 5.2% slightly higher compared to the bulk drug rhGDF-5 solution in 10 mM HCl (4.8%) all other determined values lay notably below.

Conclusion

The data demonstrate the increased stability of the rhGDF-5 formulation in acetic acid for the application in the siliconized containment compared to the formulation in HCl. For all investigated process parameters the degradation rate of the acetic acid formulation is significantly lower than the corresponding value of the standard formulation in HCl. Furthermore this experiment clearly demonstrates an advantageous effect of methionine to prevent degradation of rhGDF-5 in the formulation designed for the use in the siliconized containment.

As a result of this experiment the optimized rhGDF-5 formulation with regards to processing and stability was identified with the 50 mM acetic acid 110 mM methionine formulation of rhGDF-5. Additionally this experiment is a first prove of concept for the intended large-scale manufacturing process.

EXAMPLE 8

Dosage Conformity of Implants Coated with rhGDF-5 by Using Siliconized Containments The main objective was to get detailed information about the distribution of rhGDF-5 between the implant surface and the siliconized containment, especially in terms of reproducibility and dosage conformity. Furthermore the feasibility of different coating densities, i.e. protein doses per fixtures should be tested.

The controlled deposition of rhGDF-5 between the siliconized containment and the titanium implant was analyzed by quantifying the amount of protein on the implant as well as the residual amount of protein in the siliconized containment. To enlighten the question of controlled deposition experiments with different rhGDF-5 concentrations in the coating solution (34 µg, 122 µg and 298 µg per implant) were performed. To allow a statistical evaluation of the dosage conformity of implants coated using this method, six fixtures per dosage were coated. Afterwards the implant and the corresponding containment were analyzed separately in terms of rhGDF-5 quantity and protein degradation products. To assess the importance of the siliconization of the containment the influence regarding the rhGDF-5 distribution was additionally tested in a separately experiment were none siliconized containment were used.

Results

Concerning the necessity of using siliconized containments for the coating the obtained data shown in FIG. 8 and FIG. 9 clearly indicate the advantages, regarding the protein distribution between the containment and the implant. While for untreated containments more than 30% rhGDF-5 remains in the vial, this amount can be massively reduced down to 5% if siliconized containments were used. This effect is mostly independent from the absolute rhGDF-5 load and is reproducible for all investigated dosages (34 µg, 121.5 µg and 298 µg per fixture).

Table 4 summarizes a statistical analyzes of the dosage conformity. In spite of the fact that the used containments are handmade and differ in their dimensions, the conformity of the dosage seems to be reliable.

TABLE 4

Statistical analysis of the dosage conformity of coated implants

| Theoretical dosage [µg rhGDF-5 per implant] | Effective dosage per implant (Recovery after extraction mean value) [% of theoretical] | Standard deviation [%] | Coefficient of variation [%] |
|---|---|---|---|
| 34 (untreated) | 51.8 | 6.5 | 12.5 |
| 34 (siliconized) | 82.4 | 5.1 | 6.2 |
| 121.5 (siliconized) | 85.8 | 8.9 | 10.4 |
| 298 (siliconized) | 94.9 | 10.3 | 10.9 |

Interestingly an additional beneficial effect of the siliconized containments on the rhGDF-5 degradation can be observed. The determined rhGDF-5 degradation during the four coating setups is summarized in table 5. The comparison between untreated containments and siliconized containments (with the same coating dosage) show an approx. 1% higher rhGDF-5 degradation for the siliconized containments.

TABLE 5

Statistical analysis of the rhGDF-5 degradation of containments coated fixtures

| Sample description | rhGDF-5 degradation (Recovery after extraction mean value) [% of theory] | rhGDF-5 degradation (Caused by coating procedure) [% of theory] | rhGDF-5 degradation (Caused by coating procedure) [μg] |
|---|---|---|---|
| Coating solution for 34 μg rhGDF-5/implant | 5.1 | — | — |
| Implants coated with 34 μg rhGDF-5/implant (untreated containment) | 7.7 | 2.6 | 0.9 |
| Implants coated with 34 μg rhGDF-5/implant (siliconized containment) | 6.6 | 1.5 | 0.5 |
| Coating solution for 121.5 μg rhGDF-5/implant | 5.3 | — | — |
| Implants coated with 34 μg rhGDF-5/implant (siliconized containment) | 5.8 | 0.5 | 0.6 |
| Coating solution for 298 μg rhGDF-5/implant | 4.6 | — | — |
| Implants coated with 298 μg rhGDF-5 (siliconized containment) | 4.8 | 0.2 | 0.6 |

Further on the data show that with increasing coating dosage the percentage of rhGDF-5 degradation was suppressed from 6.6% for a dosage of 34 μg per implant down to 4.8% for a dosage of 298 μg per implant. With the knowledge of the initial quantity of the degradation of the coating solution the absolute amount of rhGDF-5 degradation caused by the coating procedure was calculated with approx. 0.5 μg per implant for siliconized containments, independently from the coating dosage. For untreated containments this value is with approx. 0.9 μg twice as high.

Conclusion

The presented data show that a reproducible coating with rhGDF-5 with regards to protein distribution between implant and containment and dosage conformity can be achieved by using siliconized containments.

EXAMPLE 9

Determination of the Homogenous Distribution rhGDF-5 Coated Implants Analyzed by Fluorescence Microscopy Because the RP-HPLC data not allow to monitor information concerning the homogeneity of the coating on the implant surface we used fluorescence microscopy to gain detailed informations of the protein distribution on the implant surface.

The homogeneity of the rhGDF-5 coating was analyzed by using a fluorescence microscope as described in example 4. The first analyzed samples were implants yielded from the previous described experiment 8 and were coated with 298 μg rhGDF-5 per implant.

To identify the parameters that are responsible for possible inhomogeneity of the protein coating we did detailed visual examinations of the drying process. For this purpose we recorded the whole process with a digital camera. Based on these results we find that air bubbles could arise from the porous surface of the implant (see FIG. 13) during lowering the pressure in the freeze-dryer.

In an additional attempt to optimize the coating conditions, we varied some parameters that have an effect on the protein distribution:
    the pressure; to allow a complete wetting in particular also inside the pores in the implant surface. We changed vacuum from a constant pressure level to a designed pulsed pressure profile.
    the position of the implant in the container upside vs. upside down, because the conical shape of the implant allows air bubbles to escape the container more easily.
    the shape of the container.

Test results with both positions of the implant in the container and optimized drying parameters are shown in FIG. 11. The pictures demonstrate, that implants, dried in up-side down position have an advantageous radial symmetric coating with some protein concentration at the taper of the implant.

The invention claimed is:

1. Method of coating of a device with a substance comprising the steps of:
    (a) providing a container having a receptacle for receiving the device to be coated, wherein the receptacle of the container is coaxially located within a container housing, the container and the receptacle being configured so that the device is coatable with the coating substance directly in the container, wherein an inner surface of the receptacle is coated with a layer of an inert, repelling material configured to increase a quantitative deposition of the coating substance on the device;
    (b) providing a solution of the coating substance within the receptacle;
    (c) inserting the device into the solution of the coating substance within the receptacle of the container, where the order of steps (b) and (c) can be reversed; and
    (d) starting isothermal drying of the device while the device remains within the solution held within the receptacle of the container, thereby removing volatile components from the solution of the coating substance.

2. The method of claim 1, wherein said substance is a pharmaceutically active substance.

3. The method of claim 2, wherein said pharmaceutically active substance is immobilized in an inorganic or organic bioresorbable material.

4. The method of claim 1, wherein said substance comprises nonactive ingredients.

5. The method of claim 1, wherein said substance comprises calcium phosphates.

6. The method of claim 1, wherein the container becomes a packaging container for the device.

7. The method of claim 1, wherein said solution is an aqueous solution or an organic solvent.

8. The method of claim 1, wherein said solution is an acid aqueous solution.

9. The method of claim 1, wherein said solution contains an antioxidant.

10. The method of claim 9, wherein said antioxidant is methionin or its derivatives.

11. The method of claim 1, wherein said device is made of metal or metal alloy.

12. The method of claim 1, wherein said device is a dental implant or a coronary stent.

13. The method of claim 1, wherein the method provides a homogeneous distribution of the coating on the device.

14. The method of claim 1, wherein said device is made of titanium or a titanium alloy.

15. The method of claim 1, wherein said device is made of calcium phosphate.

16. The method of claim 1, wherein said device is made of β-tricalcium phosphate.

17. Method of coating of a device with a substance comprising the steps of:
   (a) providing a container having a receptacle for receiving the device to be coated, wherein the receptacle of the container is coaxially located within a container housing, the container and the receptacle being configured so that the device is coatable with the coating substance directly in the container, wherein an inner surface of the receptacle is coated with a layer of an inert, repelling material configured to increase a quantitative deposition of the coating substance on the device, and wherein the container and the receptacle is a packaging container for the device;
   (b) providing a solution of the coating substance within the receptacle;
   (c) inserting the device into the solution of the coating substance within the receptacle of the container, where the order of steps (b) and (c) can be reversed; and
   (d) starting isothermal drying of the device while the device remains within the solution held within the receptacle of the container, thereby removing volatile components from the solution of the coating substance.

* * * * *